United States Patent
Striem et al.

(10) Patent No.: US 7,799,831 B2
(45) Date of Patent: Sep. 21, 2010

(54) LIPOPHILIC DIESTERS OF CHELATING AGENT FOR INHIBITION OF ENZYME ACTIVITY

(75) Inventors: Sarina Striem, Rehovot (IL); Jonathan Eduard Friedman, Rehovot (IL); Dalia Reznitsky-Cohen, Nes-Ziona (IL); Alexander Kozak, Rehovot (IL)

(73) Assignee: D-Pharm Ltd., Kiryat Weizmann Science Park Rehovot (IL)

( * ) Notice: Subject to any disclaimer, the term of this patent is extended or adjusted under 35 U.S.C. 154(b) by 861 days.

(21) Appl. No.: 10/529,028

(22) PCT Filed: Mar. 16, 2003

(86) PCT No.: PCT/IL03/00225

§ 371 (c)(1), (2), (4) Date: Mar. 24, 2005

(87) PCT Pub. No.: WO2004/028443

PCT Pub. Date: Apr. 8, 2004

(65) Prior Publication Data

US 2006/0167092 A1    Jul. 27, 2006

(30) Foreign Application Priority Data

Sep. 25, 2002   (IL) .................................. 151921

(51) Int. Cl.
*A61K 31/235* (2006.01)
*A61K 31/195* (2006.01)

(52) U.S. Cl. ..................................... 514/533; 514/564

(58) Field of Classification Search .................. 514/533, 514/564; 560/155
See application file for complete search history.

(56) References Cited

U.S. PATENT DOCUMENTS

2001/0007865 A1   7/2001   Kozak ........................ 514/143

FOREIGN PATENT DOCUMENTS

| WO | WO 95/34302 | 12/1995 |
|----|-------------|---------|
| WO | WO 97/09976 | 3/1997 |
| WO | 99/16741 | 4/1999 |
| WO | 9916741 A2 | 4/1999 |
| WO | WO 02/47674 | 6/2002 |

OTHER PUBLICATIONS

Krakovsky, M. et al., "DP-b99: A novel membrane-targeted compound active against global and focal cerebral ischemia," *Physiological Imaging of the Brain with PET*, (2001), pp. 347-352.

(Continued)

*Primary Examiner*—Taylor Victor Oh
(74) *Attorney, Agent, or Firm*—Leslye B. Davidson; Davidson, Davidson & Kappel, LLC

(57) ABSTRACT

The present invention relates to the use of lipophilic diesters of the chelating agent 1,2-bis(2 aminophenoxy)ethane-N,N,N',N'-tetraacetic acid (BAPTA) for inhibition of proteolytic activities of certain metalloproteinases and of calpain. The invention further relates to methods for preventing, treating or managing MMP-related and calpain-related diseases or disorders in mammals comprising administering to a mammal in need thereof, a pharmaceutical composition comprising a therapeutically effective amount of said lipophilic diesters of the chelating agent BAPTA.

8 Claims, 6 Drawing Sheets

OTHER PUBLICATIONS

Woessner, J.F., "Matrix metalloproteinase inhibition. From the Jurassic to the third millennium," *Ann. NY Acad. Sci.*, (1999), 878: 388-403.

Ferry, G. et al., "A zinc chelator inhibiting gelatinases exerts potent in vitro anti-invasive effects," *Eur. J. Pharmacol.*, vol. 351, No. 2 (1998), pp. 225-233.

Tetsuro Kubota, "Marimastat," *Journal of clinical and experimental medicine*, vol. 194, No. 13 (2000), p. 988.

Abel-Hamid, K. M. et al. "Mechanisms and effects of intracellular calcium buffering on neuronal survival in organotypic hippocampal cultures exposed to anoxia/aglycemia or to excitotoxins" Journal of Neuroscience, New York, NY, US, vol. 17, No. 10, May 15, 1997, pp. 3538-3553, XP002978437.

Krakovsky, M. et al. "DP-b99: A novel membrane-targeted compound active against global and focal cerebral ischemia" Physiological Imaging of the Brain with PET (2001), 347-352. Academic Press: San Diego, CA.

Krakovsky, M. et al. Abstract: "DP-b99: A novel membrane-targeted compound active against global and focal cerebral ischemia", (2001)Chemical Abstracts Service, Columbus, OH, US.

Supplementary European Search Report issued in corresponding European Patent Application No. EP 03 71 0190, Feb. 18, 2008.

LIPOPHILIC DIESTERS OF CHELATING AGENT FOR INHIBITION OF ENZYME ACTIVITY

FIELD OF THE INVENTION

The present invention relates to the use of lipophilic diesters of the chelating agent 1,2-bis(2 aminophenoxy) ethane-N,N,N',N'-tetraacetic acid (BAPTA) for inhibition of proteolytic activities of certain metalloproteinases and of calpain.

BACKGROUND OF THE INVENTION

Matrix metalloproteinases (MMPs) are extracellular zinc- and calcium-dependent proteases, which are produced in a latent form and require activation for catalytic activity. Activation occurs at the cell surface and enables MMPs to degrade components of the extracellular matrix (ECM) at specific sites in the membrane surroundings. The most studied MMPs are the gelatinases, which include MMP-2 and MMP-9 that use gelatin, Type IV collagen and fibronectin as preferred substrates. While transcription of MMP-9 genes is transactivated by cytokines and growth factors, MMP-2 is constitutively expressed and unresponsive to phorbol ester and most cytokines. MMP-2 activation is regulated by MT1-MMP, which is a membrane-anchored MMP. MMP-9 activation is regulated by a protease cascade involving plasmin and stromelysin-1 (MMP-3).

Matrix metalloproteinases are responsible for much of the turnover of matrix components and as such are involved in normal as well as in pathological processes. MMPs have an important role in maintenance and remodeling of membranes and ECM, for example, in breaking down the extracellular matrix to allow cell growth and tissue remodeling during development and recovery from injury. They also play a role in processes such as ovulation, modulation of capillary permeability and in enabling cell migration to a site of inflammation.

MMPs are involved in many pathological conditions. For example, they are associated with pathogenic mechanisms in cancer such as invasion, metastasis and angiogenesis [Reviewed by Foda and Zucker (2001) Drug Discovery Today 6: 478-482]. MMPs play a part in progression of inflammatory conditions and diseases involving degradation of extracellular matrix, such as in stroke, hemorrhage, rheumatic diseases (e.g. arthritis), Crohn's disease, asthma, and in cerebrovascular and cardiovascular disorders [Mun-Bryce and Rosenberg (1998) J. Cerebral Blood Flow Metabolism 18:1163-72; Yong et al. (1998) TINS 21:75-80; Lukes et al. (1999) Mol. Neurobiol. 19:267-284]. Members of the MMP family have also been implicated in neurological diseases and conditions as being involved in demyelination and neuro-inflammatory processes. For example, MMPs have been associated with brain damage and ischemia, Guillain-Barré, multiple sclerosis, amyotrophic lateral sclerosis and Alzheimer's disease. The current notion is that inflammation leads to the production of cytokines, chemokines, growth factors and hormones that modulate MMPs production. Activation of MMPs and plasminogen activators (PAs) is an important regulatory step in the inflammatory response.

Members of another family of metalloproteinases, identified as "A Disintegrin And Metalloproteases" (ADAM), have, like members of the MMP family, multiple domains including a zinc-dependent catalytic domain and a N-terminus pro-domain that is responsible for maintaining the enzyme in an inactive state [Moss et al. (2001) Drug Discovery Today 6: 417-426]. It was shown that members of the ADAM family are involved in several different processing events including cleavage of substrates off the cell membrane surface (a phenomenon termed "shedding"). One member of the ADAM family is the TNFα-Converting Enzyme (TACE). TACE is found on the cell surface where it processes the membrane-bound TNFα, a pro-inflammatory cytokine, to its mature soluble form. Soluble TNFα, which is released in inflammatory conditions, can induce apoptosis. For example, TNF induces secretion and activation of MMP-9 in macrophages and glial cells and causes neuronal cell death in neuroinflammatory diseases and following brain injuries. TNF has also been shown to play a role in pathological conditions such as rheumatoid arthritis.

As potentially highly toxic proteolytic enzymes, the matrix metalloproteinases are tightly regulated at multiple stages, as follows:

i) Gene transcription—most MMPs are not constitutively expressed, but their transcription is controlled by various cytokines (e.g. IL-1, TNF) and growth factors (e.g. TGF-β, retinoic acid, FGF).

ii) Pro-enzyme activation—MMPs are normally produced in a latent form (pro-MMP) including a propeptide segment that generally must be removed to activate the enzyme.

iii) Inhibition of enzyme activity—There are at least four endogenous MMP-inhibitors known as tissue inhibitors of metalloproteinases (TIMPs), which bind to the enzyme and block its activity. Another known natural inhibitor of MMPs is the serum proteinase inhibitor α-macroglobulin.

Several synthetic inhibitors of MMPs have been described in various publications in the scientific and patent literature. Currently known inhibitors mainly include synthetic peptides and chelating agents [reviewed by Woessner J F Jr. in Ann N.Y. Acad. Sci. (1999) 30:388-403].

Some synthetic inhibitors of the MMP active site are peptidomimetics based on the sequence of peptides cleaved in collagen [Masui et al. (1977) Biochem Med. 17:215-21). Peptidic agents based on conserved peptide sequence derived from the pro-segment of human collagenase IV are disclosed by Stelter-Stevenson et al. [Am J Med Sci. (1991) 302:163-70] and in U.S. Pat. No. 5,270,447 to Liotta et al. Synthetic peptides isolated from phage display peptide libraries and cyclic peptides with MMP inhibitory activity are described by Koivunen et al. [Nat. Biotechnol (1999) 17: 768-74].

N-hydroxyformamide peptidomimetics useful as TACE and MMPs inhibitors are disclosed by Musso et al. [Bioorg Med Chem Lett (2001) 11: 2147-51].

Other polypeptides and peptoid compounds useful as metalloproteinase inhibitors are disclosed in U.S. Pat. Nos. 4,263,293 and 4,297,275 to Sundeen et al., in U.S. Pat. Nos. 4,371,465, 4,371,466 and 4,374,765 all issued to McGregor, and in U.S. Patent Publication No. 2002/0090654 to Langley et al.

Non-peptidic MMP-inhibitory compounds are disclosed in U.S. Pat. No. 4,950,755 to Witiak et al. and in U.S. Pat. No. 5,866,570 to Liang et al.

MMPs inhibitors comprising targeting moieties and chelators are disclosed in International Patent Publication No. WO 01/60820 of Dupont Pharmaceuticals Company, and in International Patent Publication No. WO 02/053173 to Kimberly-Clark Worldwide, Inc.

Matrix metalloproteinases as well as other members of the ADAM family are inhibited by chelating agents. Most of these chelating agents are natural and synthetic hydroxamate compounds and derivatives thereof such as succinyl hydroxamate, sulfonamide hydroxamate etc. [reviewed by Woessner, J. F. Jr. (1999) in Annals New York Academy of Sciences 30: 388-403]. For example, the synthetic hydroxamates batimastat (BB-94; Invest New Drugs (1996) 14:193-202) and its orally bioavailable analogue marimastat have been shown to inhibit spread and growth of malignant tumors in animals. These compounds are currently examined in advanced clinical trials.

Among the compounds that have been shown as MMPs inhibitors are also antibiotics such as tetracyclines and their chemically modified analogs (Golub et al. (1983) J Periodontal Res. 18:516-26; U.S. Pat. No. 4,704,383 to McNamara et al.; U.S. Pat. No. 5,837,696 to Golub et al.].

Most of the above-mentioned agents are non-specific inhibitors of metalloproteinases and other metal-ion dependent proteases.

Calpains are members of another family of proteases. These are cytosolic enzymes which are calcium-dependent cysteine proteases. Calpains predominantly exist within cells as inactive proenzymes and are converted into their active forms in the presence of elevated intracellular calcium levels. Upon binding of calcium, the precursor enzyme goes through a self-digestion process that results in release of the activated calpain.

A wide range of proteins serves as substrates for calpain including cytoskeletal, membrane and regulatory proteins. Calpain participates in a number of normal cellular signal transduction systems as well as in pathological conditions. For example, calpain activation has been associated with ischemia and neuronal cell death such as those caused by stroke and traumatic brain and spinal cord injuries [Bartus et al. (1995) Neurol. Research 17:249-258]. Calpain proteolytic activity has also been implicated in several neurodegeneration diseases and conditions, including Alzheimer's Disease, Parkinson's disease, Huntington's disease and Pick's disease.

Presently known natural and synthetic calpain inhibitors, including both peptidic and non-peptide molecules, are reviewed by Wang and Yuen ["Calpain inhibition: an overview of its therapeutic potential" in Trends Pharm. Sci. (1994) 15, 412-419] and by Donkor ["A survey of calpain inhibitors" in Curr. Med. Chem. (2000) 7:1171-88]. Known calpain inhibitors include polypeptides which mimic peptide sequences of the natural inhibitors calpastatin and kininogen [for review, see Wang and Yuen (1994) Trends Pharm. Sci. (1994) 15, 412-419].

Compounds which are sulfonamide derivatives and ketone derivatives that possess inhibitory activity against cysteine proteases are disclosed, respectively, in U.S. Pat. Nos. 5,506,243 and 5,639,783 both to Ando et al. Calpain inhibitors which are di-peptide alpha-keto esters, alpha-keto amides and alpha-keto acids are described by Li et al. [J. Med Chem (1993) 36: 3472-80]. Several other classes of calpain inhibitors are disclosed by Bartus et al. in International Patent Publication no. WO 92/11850.

Most commercially available calpain-inhibitors are compounds based on peptide structures that interact with the substrate-binding site of the enzyme. Many of these compounds are non-specific and inhibit a wide variety of proteases in addition to calpain. Moreover, most of the known inhibitors that were active in vitro, were found ineffective in inhibiting calpain in-vivo, in particular in the CNS, as being poor membrane permeants. Furthermore, almost all MMPs-inhibitors tested for treating pathological inflammatory conditions or cancers failed in in-vivo clinical studies.

Thus, there remains a long-felt need for effective, non-toxic agents which are specific inhibitors of critical proteases such as the MMPs and calpain.

BAPTA-Diesters

Stable lipophilic diesters of the divalent metal ion chelator 1,2-bis(2 aminophenoxy)ethane-N,N,N',N'-tetraacetic acid (BAPTA) have been disclosed in the International Patent Publication No. WO 99/16741 of the same applicant. Also disclosed in this publication is the use of these compounds in pharmaceutical compositions useful for treating diseases and disorders related to excess of divalent metal ions. Among these diseases and disorders are ischemia, stroke, epilepsy and neurodegenerative diseases such as Alzheimer's disease and Parkinson's disease.

At that time, however, the mechanism by which these chelating agents exert their neuroprotective effects has not been elucidated or disclosed. No indication or suggestion for the cellular targets affected by these chelators has been mentioned in the WO 99/16741 or any other publication.

SUMMARY OF THE INVENTION

It has now been found, in accordance with the present invention, that certain diesters of the chelating agent 1,2-bis(2 aminophenoxy)ethane-N,N,N',N'-tetraacetic acid (hereinafter denoted as "DP-BAPTAs") are capable of inhibiting enzymatic activities of the proteases matrix metalloproteinase (MMP), calpain and TNFα-Converting Enzyme (TACE).

Accordingly, the present invention provides, in one aspect, a method of inhibiting protease activity, said protease being selected from metalloproteinase and calpain, the method comprising exposing cells to inhibiting amount of a compound of the general formula (I):

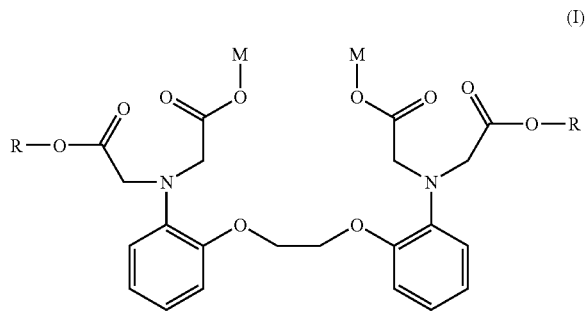

(I)

wherein

R is saturated or unsaturated alkyl, cycloalkyl, arylalkyl or cycloalkyl-alkyl radical having from 1 to 28 carbon atoms which may be interrupted by any combination of 1-6 oxygen and/or nitrogen atoms, provided that no two oxygen atoms or an oxygen and a nitrogen atom are directly connected to each other; and M denotes a hydrogen or a physiologically acceptable cation.

In addition, certain compounds disclosed herein are novel and in themselves constitute an aspect of the present invention. These compounds include the compound of the general formula (I) wherein R is 2-benzyloxyethyl. Thus, according to another aspect of the invention, there is provided a compound of the general formula (I) which is 1,2-bis(2-aminophenoxy)ethane, N,N'-di(2-benzyloxyethyl acetate), N,N'-acetic acid and salts thereof. Also provided by the invention are pharmaceutical compositions comprising a therapeutically effective amount of said compound and a pharmaceutically acceptable carrier or excipient.

According to currently preferred embodiments of the invention, the useful compounds for inhibiting the MMP-9 activity are the following compounds and physiologically acceptable salts thereof:

1,2-bis(2-aminophenoxy)ethane, N,N'-di(2-octoxyethyl acetate), N,N'-diacetic acid (denoted herein DP-b99), 1,2-bis(2-aminophenoxy)ethane, N,N'-di(2-octodecyloxyethyl acetate), N,N'-diacetic acid (denoted herein DP-b109), 1,2-bis(2-aminophenoxy)ethane, N,N'-di(2-benzyloxyethyl acetate), N,N'-acetic acid (denoted herein DP-b440), 1,2-bis(2-aminophenoxy)ethane, N,N'-di(2-dodecyloxyethyl acetate), N,N'-diacetic acid (denoted herein DP-b460), 1,2-bis(2-aminophenoxy)ethane, N,N'-di[2-(2-dodecyloxyethoxy)-ethyl acetate], N,N'-diacetic acid (denoted herein DP-b458), and Currently most preferred compounds for inhibiting calpain activity are 1,2-bis(2-aminophenoxy)ethane, N,N'-di(2-octoxyethyl acetate), N,N'-diacetic acid (DP-b99) and 1,2-bis(2-aminophenoxy)ethane, N,N'-di(2-octodecyloxyethyl acetate), N,N'-diacetic acid (DP-109) and physiologically acceptable salts thereof.

In another aspect of the invention, there are provided methods for preventing, treating or managing diseases and pathological conditions associated with damaging MMP and/or calpain activities. The methods comprise administering to a mammal in need thereof, a pharmaceutical composition containing as an active ingredient a therapeutically effective amount of a compound of the above-mentioned general formula (I).

In yet another aspect of the invention, there is provided the use of a compound of the general formula (I) for the preparation of a medicament for inhibiting the activity of a protease selected from metalloproteinase, calpain and TACE.

The present invention further provides methods and the use of the compounds of the general formula (I) for the treatment of MMP- or calpain-related diseases, disorders or conditions, which may be selected from the group consisting of cancer (including metastasis cancer), angiogenesis-dependent diseases (e.g. cancerous tumors, arthritis, psoriasis, macular degeneration, chronic inflammation and diabetic retinopathy), ischemic or hypoxic tissue damage, oxidative injury, stroke, trauma, inflammatory conditions and diseases (e.g. arthritides, rheumatoid arthritis, osteoarthritis, restenosis, asthma, psoriasis, systemic lupus erythematosus, inflammatory bowel syndrome, Crohn's disease, gingivitis, periodontitis, meningitis, tropical spastic paraparesis, sepsis, bullous skin disorders, acne and inflammation due to infectious diseases), atherosclerosis, thrombotic disorders, arthritis, osteoporosis, diabetes, hemorrhage, autoimmune diseases, rheumatic diseases, ocular pathologies and retinopathies (e.g. diabetic retinopathy, glaucoma, macular degeneration, cataract, retinal detachment and retinal tears), burns, chronic wounds (e.g. ulcers), neurological and neurodegenerative diseases and disorders (e.g. multiple sclerosis (MS), Alzheimer's disease (AD), motor neuron disease (MND), amyotrophic lateral sclerosis (ALS), Guillain-Barré, Parkinson's disease, Huntington disease, Pick's disease, dementia syndrome, vascular dementia, multiple infarct dementia, HIV-induced neural disorders, brain ischemia (both global and focal ischemia) and neuronal tissue trauma), migraine, cerebrovascular and cardiovascular disorders.

The methods of treatment in accordance with the invention may further comprise treating the patient with additional therapeutic treatment which may be carried out concurrently with, preceding or subsequent to the administration of the pharmaceutical composition comprising a compound of the general Formula (I).

It is important to note that not any chelator can inhibit the activity of the tested proteases. In contrast to the effect of DP-BAPTA compounds, the closely related known chelators, BAPTA and BAPTA-AM, at doses similar to DP-BAPTA, did not inhibit MMP-9 activity. In fact, BAPTA-AM even slightly enhanced the MMP-9 activity.

Another point to emphasize is that, under the experimental conditions employed, the tested DP-BAPTAs inhibited calpain and MMP-9 proteolytic activities, however no such effect could be demonstrated for the other gelatinase tested, MMP-2.

Further objects of the present invention will become apparent to those skilled in the art upon further review of the following disclosure, including the detailed descriptions of specific embodiments of the invention.

DETAILED DESCRIPTION OF THE INVENTION

Figure 1A:
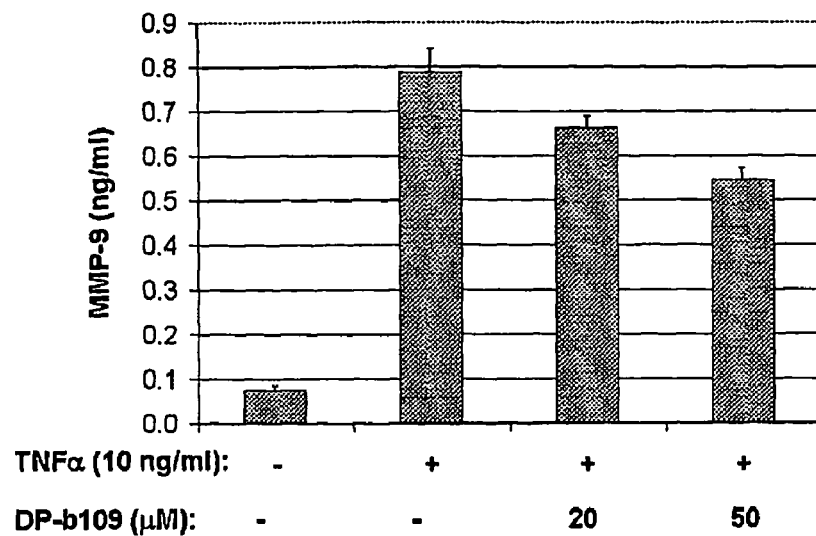
FIGS. 1A-B depict total amount of MMP-9 enzyme (A) and the MMP-9 enzymatic activity (B) in the conditioned media collected from cultured A-172-glioma cells treated with 10 ng/ml TNFα, in the absence or presence of 20 μM or 50 μM DP-b109, as indicated.

The synthesis and some utilization of stable lipophilic diesters of BAPTA (DP-BAPTAs) have been disclosed in the International Patent Publication No. WO 99/16741 of the same applicant, the teaching and disclosure of which are expressly incorporated herein in their entirety by reference. In the WO 99/16741 publication, the neuroprotective effects of DP-BAPTAs were demonstrated in neuronal cell cultures in-vitro, and in ischemia model systems in-vivo. However, the effect of the DP-BAPTA molecules on activities of specific enzymes has not been taught or suggested in that or any other publication. Accordingly, it was neither taught, recognized or suspected that these compounds could be effectively use for the treatment of MMP- and calpain-related diseases and disorders as disclosed in the present application.

It is now disclosed, for the first time, that certain diesters of the chelating agent BAPTA are capable of inhibiting the activity of calpain and of certain proteases of the ADAM family, and in particular inhibiting the activity of matrix metalloproteinase-9 (MMP-9).

The useful compounds in accordance with the invention are of the general formula (I) as described above. It is to be understood that within the scope of the invention are included also pharmaceutically acceptable salts of the compounds of the general formula (I) including organic and inorganic cations, as well as various solvates, including hydrates, and other active forms of the compounds of the general formula (I).

Currently preferred compounds for inhibiting MMP or calpain activities are diesters of BAPTA with alkyl chains comprising from around 8 to 20 carbon atoms. The alkyl chains may be saturated or unsaturated alkyls including one or more double bonds and/or a triple bond. According to preferred embodiments of the invention, the alkyl chain is interrupted by from 1 to 3 oxygen atoms. According to most preferred embodiments, the R moiety of a compound of the general formula (I) includes a monoalkyl ether of ethylene glycols, preferably mono-, di- or tri-ethylene glycols.

The alkyl residue at position R of the compound of the general formula (I) may consist of or include cyclic elements that may be aromatic or non-aromatic ring structures. Preferably the cyclic elements have 5 or 6 carbon atoms.

Currently preferred cyclic R radicals comprise aromatic ring which is a phenyl residue. Other currently preferred cyclic elements included at position R are saturated or unsaturated cyclopentyl, cyclohexyl or cycloheptyl. The cyclic elements may be directly linked to the carboxy moiety of the compound of the general formula (I), or linked via a saturated or unsaturated alkyl chain that may include one or more oxygen and/or nitrogen atoms.

Preferably, the compound of the general formula (I) includes a monovalent cation at position M. Suitable pharmaceutically acceptable cations may include, but are not limited to, $H^+$, $Na^+$, $Li^+$, $K^+$, $NH_4^+$ and mono-alkylammonium. Also divalent cations may be included at position M. The choice of the preferred cation at position M of the general formula (I) depends on the intended therapeutic use of the compound, as well as on the specific formulation and route of administration employed. A person skilled in the art will be able to select the appropriate cation as required for the optimal pharmaceutical compositions and way of administration chosen in each particular treated case.

One of the most preferred DP-BAPTA compounds is 1,2-bis(2-aminophenoxy)ethane, N,N'-di(2-benzyloxyethyl acetate), N,N'-acetic acid (DP-b440), where the R moieties of the compound of the general formula (I) include an alkylaryl moiety. This compound was disclosed generally in the WO 99/16741 publication, but was not specifically claimed and not individually tested.

It has now been shown by the inventors of the present invention that DP-BAPTAs can attenuate or block both basal MMP-9 activity and TNFα- or PMA-induced activation of MMP-9. DP-BAPTAs can also inhibit calpain activity. Hence, DP-BAPTAs may be useful in reducing deleterious protease activities in pathological conditions due, for example, to ischemia and inflammatory responses. Accordingly, DP-BAPTA compounds may be useful in preventing, treating or managing diseases and pathological conditions associated with harmful activities of matrix metalloproteinases or calpains.

It is important to note that while MMP-9 activity was significantly inhibited by the DP-BAPTA compounds, such inhibitory activity could not be demonstrated with the related chelators tested, namely 1,2-bis(2-aminophenoxy)-ethane-N,N,N',N'-tetra-acetic acid (BAPTA) or 1,2-bis(2-aminophenoxy)ethane-N,N,N',N'-tetra-acetic acid acetoxymethyl ester (BAPTA-AM).

The DP-BAPTA compounds in accordance with the invention may be useful in the treatment of a whole range of indications which involve degradation processes carried out or mediated by MMPs, TACE or calpain. These indications include, but are not limited to, diseases and conditions due to neuronal ischemia (e.g. global brain ischemia and focal brain ischemia), cardiac ischemia, trauma, stroke and inflammatory conditions including neuroinflammatory diseases and disorders, rheumatic and autoimmune diseases, neurological, cerebrovascular and cardiovascular diseases and disorders. The DP-BAPTA compounds may also be useful in compositions and methods for enhancing wound healing such as, for example, in burns and in chronic wounds (e.g. ulcers).

A large amount of data has been accumulated which show MMP- and/or calpain-involvement in progression of diseases and conditions where inflammatory processes are implicated. These pathological conditions include, but are not limited to, rheumatoid diseases (e.g. rheumatoid arthritis and osteoarthritis), asthma, psoriasis, systemic lupus erythematosus, inflammatory bowel syndrome, Crohn's disease, gingivitis, periodontitis, meningitis, tropical spastic paraparesis, sepsis, bullous skin disorders, acne and inflammation due to infectious diseases.

The infectious diseases may include, but are not limited to, infectious diseases caused by any type of microorganism such as bacteria, fungi (e.g. candidiatis, aspergilosis) and viruses (e.g. herpes viruses-related disorders, HIV-related diseases), by parasites (e.g. malaria, amebiasis) or by prions (e.g. Creutzfeld-Jacob Disease).

Inhibitors of MMPs or calpain can reduce proteolytic damage to tissues such as that caused during inflammatory processes. For example, may limit brain-blood-barrier (BBB) breakdown, inhibit neuroinflammation (e.g. as in meningitis), reduce damage associated with brain or cardiac ischemic injuries, and may diminish proteolytic effects caused by insults such as oxidative stress, burns, infections and central (CNS) and peripheral nervous system (PNS) injuries due to physical causes (e.g. trauma).

Elevated MMP or calpain activity has been linked to several neurodegenerative diseases and conditions including, but not limited to, multiple sclerosis (MS), motoneuron disease (MND), amyotrophic lateral sclerosis (ALS), Alzheimer's disease, Guillain-Barré syndrome, Parkinson's disease, Huntington's disease, Pick's disease, dementia syndrome, vascular dementia, multiple infarct dementia, HIV-induced neural disorders, brain ischemia (both global and focal ischemia) and neuronal tissue trauma.

MMPs have also been associated with pathological conditions such as ischemic or hypoxic tissue damage, oxidative damage, osteoporosis, hemorrhage, arterial restenosis, cardiovascular disorders (e.g. ischemic myocardiac infarction) as well as with various ocular pathologies and retinopathies including diabetic retinopathy, glaucoma, macular degeneration, cataract, retinal detachment and retinal tears.

Cancer is another major disease where it has been shown that proteolytic activities of metalloproteinases contribute to the progression of the disease. MMPs are involved in spread of cancer, and in particular facilitating the metastasis state of the disease. MMP-2 and MMP-9 are involved in the breakdown of Type IV collagen, which is a major component of basement membrane, and as such may be key factors in processes involving membrane degradation, for example, in angiogenesis and in tumor invasion and metastasis. Indeed, positive correlation has been found between tumor progression and expression of members of the MMP family. For example, increased expression of MMP-2 and MMP-9 genes has been associated with malignancies of gliomas.

A number of factors are important in the progression of malignancies. One of the crucial factors is angiogenesis, which is believed to be fundamental for primary tumor growth, tumor progression and metastasis. The first step in the mechanism of angiogenesis involves degradation of basement membrane so to facilitate the growth of a new capillary sprout. Thus, degradation and remodeling of the ECM are essential processes for the mechanism of angiogenesis, and methods of inhibiting these processes may be beneficial in blocking angiogenesis and hence diminishing malignancies.

Angiogenesis is also important in a number of other pathological processes, including arthritis, psoriasis, diabetic retinopathy, chronic inflammation, scleroderma, hemangioma, retrolental fibroplasia and abnormal capillary proliferation in hemophiliac joints, prolonged bleeding etc. MMP-inhibitors are expected to be useful for the treatment of these angiogenic-associated diseases.

The inability to control metastasis presents a major problem, as metastases are the leading cause of death in patients with cancer. To date, there is no satisfactory treatment for preventing or limiting metastasis growth. Thus, the use of the DP-BAPTA compounds in accordance with the present invention for inhibiting MMPs, and in particular for inhibiting the MMP-9 protease activity, may be beneficial in this respect.

The cancer subjected to treatment with DP-BAPTAs may include any type of tumors and neoplastic growths that may be benign or malignant growths including primary tumors as well as secondary tumors. The terms "cancer" and "neoplastic growth" are interchangeably used in the specification and claims and mean to cover all kinds of pathological uncontrolled cell growths including invasive and non-invasive neoplasms, solid and non-solid tumors, and including remote metastases.

The term "treatment" as used herein means to include therapeutic procedures aiming at preventing, ameliorating, palliating, inhibiting or delaying the onset and/or development and/or progression of a pathological condition or improving its manifestations.

It should be understood that the therapeutic activity of the compounds of the general formula (I), as disclosed and claimed herein, is irrespective of the exact mechanism of action of these compounds and is not meant to be limited to any particular mode of action by which these molecules exert their beneficial effect(s).

In accordance with the methods of the invention, a pharmaceutical composition comprising a therapeutically effective amount of a compound of the general Formula (I) is administered to a patient in need thereof.

The administered pharmaceutical composition may include a compound(s) of the general Formula (I) as the sole active ingredient, or may include said compound(s) in combination with one or more additional agents known to be effective in the treatment of a particular disease or disorder.

The compound(s) of the general Formula (I) and the additional therapeutically active agent(s) may be included in the same pharmaceutical composition or may be administered in separate compositions. Furthermore, the use of DP-BAPTA in combination with another therapeutically active agent (or another therapeutic means) may be concurrently or not. The methods of the invention include administration of the DP-BAPTA compound(s) either at the same time, preceding or following exposure to the additional therapeutic agent or procedure.

Additional agents that may be used in combination with the DP-BAPTA compounds may be therapeutic and prophylactic drugs, hormones, immuno-modifying agents etc. and may include other chelating agents, proteins, peptides, carbohydrates, lipidic molecules, DNA and RNA sequences etc.

These agents may be selected from, but are not limited to, anti-neoplastic, anti-proliferative, anti-inflammatory, antibiotic, anti-viral, anti-microbial, anti-mycotic, anti-allergic, cardiovascular agents, anti-convulsant, anti-depressant, anti-psychotic, analgesic, neurological agents, neuroprotective agents and bioactive peptides and proteins such as neurotransmitters, immuno-modulators, growth factors, hormones, antibodies etc.

For example, in the case of treating cancer, the DP-BAPTA compound(s) may be used alone or in combination, concurrently or not, with additional anti-cancer treatment. The additional anti-cancer treatment may include, but is not limited to, chemotherapy, irradiation therapy, immunotherapy, genetic therapy, surgery or any other anti-cancer treatment as known in the art. The additional treatment may be carried out concurrently with or consecutively to the administration of the compounds of the general formula (I), namely the additional treatment may be applied concurrently or successively, either preceding or subsequent to the administration of the compound of the general formula (I). The time interval between the two treatments and the overall regimen will be determined by a person skilled in the art taking into account the specific treated disease and the particular condition and response of the treated individual to the treatment.

Any anti-cancer drug that is suitable for use in chemotherapy procedures may be applied in combination with the compound of the general formula (I). Suitable anti-cancer drugs may include, but are not limited to, alkaloids (e.g. taxol, vinblastine, vindesine and vincristine), alkylating agents such as alkyl sulfonates, aziridines, ethylenimines, methylmelamines, nitrogen mustards (e.g. cyclophosphamide) and nitrosoureas, antibiotics and analogs (e.g. aclacinomycin, actinomycin, anthramycin, daunorubicin and doxorubicin), antimetabolites such as folic acid analogs (e.g. Tomudex®), purine and pyrimidine analogs and platinum complexes (e.g. carboplatin, cisplatin, miboplatin and oxaliplatin).

The combination treatment with additional therapeutic procedures may be beneficial also in treatment of other diseases and disorders. For example, in treatment of inflammatory, neuro- or cardiovascular conditions where the administration of the DP-BAPTA compounds may be in combination with (either concurrently, preceding or subsequent to) surgery and/or treatment with another medicament or therapeutic agent (e.g. antibiotics, antibodies etc.) to remove or kill infectious agents or other pathogenic elements.

It will be readily apparent to those of ordinary skill in the art that a large number of other beneficial drugs, reagents, means or procedures may be useful in the treatment of particular pathological conditions. Pharmaceutical compositions including these therapeutically effective agents and methods applying them or other medical procedures are also included within the scope of the invention as compositions and methods useful in combination with the compounds of the general formula (I). The exact protocol and the additional medicament or therapeutic procedure used, will be determined by a person skilled in the art taking into consideration the particulars of the specific medical condition treated, e.g. the stage of the disease or disorder, its severity and progression, as well as the condition of the patient.

The pharmaceutical compositions comprising the compound of the general formula (I) may be in a liquid, aerosol or solid dosage form, and may be formulated into any suitable formulation including, but not limited to, solutions, suspensions, micelles, emulsions, microemulsions, aerosols, ointments, gels, suppositories, capsules, tablets, and the like, as will be required for the appropriate route of administration.

Any suitable route of administration is encompassed by the invention including, but not being limited to, oral, intravenous, intraperitoneal, intramuscular, subcutaneous, inhalation, intranasal, topical, rectal or other known routes. In preferred embodiments, the useful pharmaceutical compositions are orally or intravenously administered. The dose ranges are those large enough to produce the desired proteinase inhibitory effect. The dosing range varies with the specific DP-BAPTA used, the treated pathological condition and the route of administration and is dependent on the additional treatment procedure, if such additional treatment is applied.

The dosage administered will also be dependent upon the age, sex, health, weight of the recipient, concurrent treatment, if any, frequency of treatment and the nature of the effect desired. The specific dosage, regimen and means of administration will be determined by the attending physician or other person skilled in the art.

The Invention will now be illustrated by the following non-limiting examples.

EXAMPLES

Example 1

Synthesis of BAPTA Diesters of Alkyl or Alkylaryl and Salts Thereof

Synthesis of disodium or calcium salts of some diesters of 1,2-bis(2-aminophenoxy)ethane-N,N,N',N'-tetraacetic acid (DP-BAPTA) was carried out in three steps as follows:

Step 1. Preparation of an Anhydride of BAPTA:

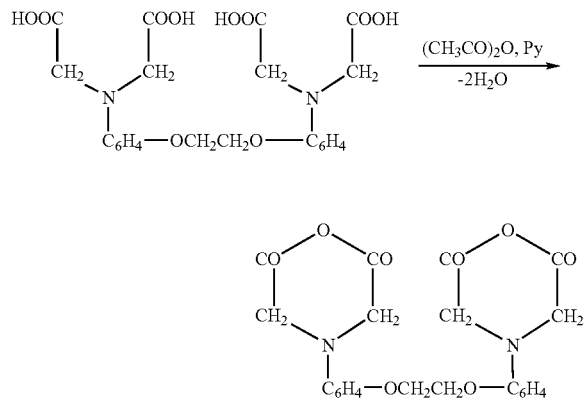

Step 2. Preparation of BAPTA Diester:

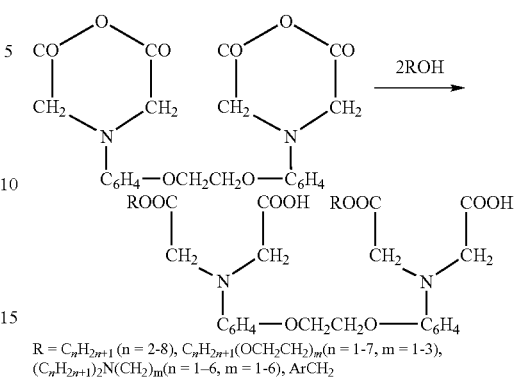

Step 3. Preparation of Disodium or Calcium Salt of the Diester of BAPTA:

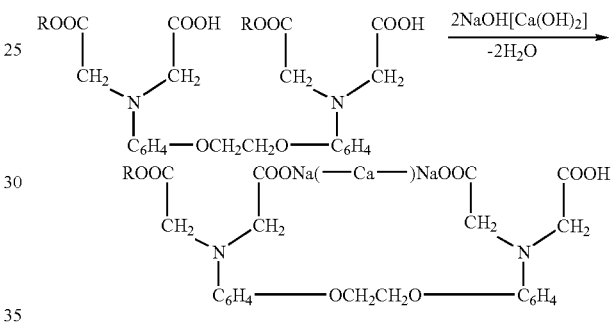

Step 1. Preparation of BAPTA Anhydride

BAPTA (24 gr., 0.05 mol), pyridine (8 gr., 0.1 mol) and acetic anhydride (95 ml, 1.0 mol) are introduced into a round-bottom single-neck flask (500 ml), equipped with a reverse condenser (water cooling) and magnetic stirrer. The reaction mixture is heated at 90° C. for 5 hours with vigorous stirring by magnetic stirrer. The temperature is then decreased to 50° C. and heating is continued at this temperature for 10 hours longer. At the end of the 10-hour period the reaction mixture is cooled to room temperature and the precipitate is extracted by filtration. The precipitate is then washed four times with ethyl acetate (50 ml each wash) and twice with ether (60 ml each wash). The precipitate is dried under vacuum at 50° C. for 6-8 hours. The product is a BAPTA anhydride. Yield 80% (17.6 g.). White solid. M.p. 148-149° C.

Analyses: TLC. The compound decomposed in the course of analysis.

$^1$H NMR ($C_6D_5NO_2$), δ (ppm): 4.40 (s, 8H), 4.47 (s, 4H) and 6.85-7.01 (m, 8H).

IR: 1762.9 $cm^{-1}$ (s), 1820.7 $cm^{-1}$ (s).

Elemental. $C_{22}H_{20}O_8N_2$. Calculated: C, 60.00%; H, 4.54%; N, 6.36%; Found: C, 59.60%; H, 4.66%; N, 6.20%.

Step 2. Preparation of Alkyl or Aryl Diester of BAPTA

The BAPTA anhydride of step 1 (10 g, 0.023 Mol) and corresponding absolute alcohol (300 ml) are introduced, under argon atmosphere, into a round-bottom single-neck flask, equipped with reverse condenser and magnetic stirrer. The mixture is heated in an oil bath at 90° C. (for methyl and ethyl diesters at 70° C.) with vigorous stirring. After 6 hours about half of the alcohol is distilled from the reaction mixture (high molecular alcohols are distilled under vacuum). The obtained mixture is cooled to 0° C. and kept at this temperature for 5-8 hours. The precipitate is separated from the solution by filtration (glass filter N4) under vacuum and is washed 3-4 times with about 40 ml of ethanol, followed by three washes (100 ml each) of ethyl acetate and finally with three washes (150 ml each) of diethyl ether. The product is dried under vacuum for 8 hours.

The chemical/physical specifications of synthesized diesters of BAPTA are presented hereinbelow:

Ethyl diester of BAPTA. Yield 90% (11 g.). White powder. M.p. 161-162° C. TLC analysis. Silica gel 60 on aluminum sheet. Eluent is mixture of chloroform with methanol and water (80:20:1.5 v/v). For indication the chromatogram is sprayed by the indicator spray and then is charred at 350-400° C. Composition of indicator spray is 4-methoxybenzaldehyde (10 ml), ethanol (200 ml), 98% $H_2SO_4$ (10 ml) and glacial acetic acid (2 ml). One spot. $R_f$ 0.3.

$^1$H NMR ($CD_3OD$). δ (ppm): 1.05-1.11 (t, 6H), 3.91-4.00 (dd, 4H), 4.05 (s, 4H), 4.14 (s,4H), 4.27 (s, 4H), 6.83-6.96 (m, 8H).

Elemental. $C_{26}H_{32}O_{10}N_2$. Calculated: C, 58.64%; H, 6.03%; N, 5.26%. Found: 58.00%; H, 6.00%; N, 5.09%.

Propyl diester of BAPTA. Yield 90% (11.5 g.). White powder. M.p. 187° C. TLC analysis. Conditions of the analyses of diethyl and dipropyl esters of BAPTA are analogous. One spot. $R_f$ 0.35.

$^1$H NMR [($CD_3$)$_2$SO], δ(ppm): 0.71-0.77 (t, 6H), 1.38-1.47 (m, 4H), 3.80-3.85 (t, 4H), 4.00 (s, 4H), 4.13 (s, 4H), 4.20 (s, 4H), 6.70-6.96 (m, 8H).

Elemental. $C_{28}H_{36}O_{10}N_2$. Calculated: C, 60.00%; H, 6.43%; N, 5.00%; Found: C, 60.25%; H, 6.77%, H, 5.08%.

Iso-propyl diester of BAPTA. Yield 80% (10.2 g.). White powder. M.p. 181-182° C. TLC analysis. Silica gel 60 $F_{254}$ on aluminum sheet. Eluent: chloroform:methanol (65:30, v/v). For indication the chromatogram is sprayed by the indicator spray and then is charred at 350-400° C. The composition of indicator spray is 4-methoxybenzaldehyde (10 ml), ethanol (200 ml), 98% sulfuric acid (10 ml) and glacial acetic acid (2 ml). One spot. $R_f$ 0.72.

$^1$H NMR [($CD_3$)$_2$SO], δ (ppm): 1.07-1.09 (d, 12H), 4.00 (s, 4H), 4.08 (s, 4H), 4.22 (s, 4H), 4.78-4.85 (m, 2H), 6.71-6.98 (m, 8H).

Elemental analysis. $C_{28}H_{36}O_{10}N_2$. Calculated: C, 60.00%; H, 6.43%; N, 5.00%. Found: 59.78%; H, 6.50%; N, 5.00%.

Butyl diester of BAPTA. Yield 90% (12.1 g.). White powder. M.p. 183° C. TLC analysis. Conditions of analyses of diethyl and dibutyl esters of BAPTA are analogous. One spot. $R_f$ 0.42.

$^1$H NMR [($CD_3$)$_2$SO]. δ ppm): 0.74-0.80 (t,6H), 1.09-1.18 (m, 4H), 1.33-1.39 (m, 4H), 3.80-3.86 (t, 4H), 3.98 (s,4H), 4.10 (s, 4H), 4.17 (s, 4H), 6.69-6.92 (m, 8H).

Elemental. $C_{30}H_{40}O_{10}N_2$. Calculated: C, 61.22%; H, 6.80%; N, 4.76%. Found: C, 61.54%; H, 7.10%, 5.03%.

Heptyl diester of BAPTA. Yield 70% (10.8 g.). White powder. M.p. 146-147° C.

TLC analysis. Conditions of analysis of ethyl and heptyl diesters of BAPTA are analogous. One spot. $R_f$ 0.50.

$^1$H NMR [($CD_3$)$_2$SO]. δ (ppm): 0.79-0.84 (t, 6H), 1.08-1.17 (broad s, 16H), 1.34-1.43 (m, 4H), 3.79-3.87 (t, 4H), 3.98 (s, 4H), 4.13 (s, 4H), 4.17 (s, 4H), 6.67-6.92 (m, 8H).

Elemental: $C_{36}H_{52}O_{10}N_2$. Calculated: C, 64.29%; H, 7.74%; N, 4.16%. Found: C, 64.37%; H, 7.82%; N, 3.88%.

Octyl diester of BAPTA. Yield 70% (11.3 g.). White powder. M.p. 155° C. TLC analysis. Conditions of analyses of diethyl and dioctyl esters of BAPTA are analogous. One spot. $R_f$ 0.55.

$^1$H NMR [($CD_3$)$_2$SO], δ (ppm): 0.81-0.86 (t, 6H), 1.19-1.23 (broad s, 20H), 1.29-1.34 (m, 4H), 3.83-3.87 (m, 4H), 3.98 (s, 4H), 4.11 (s, 4H), 4.19 (s, 4H), 6.80-6.84 (m, 8H).

Elemental: $C_{38}H_{56}O_{10}N_2$. Calculated: C, 65.14%; H, 8.00%; N, 4.00%. Found: C, 64.91%; H, 8.20%; N, 3.76%.

Benzyl diester of BAPTA. Yield 70% (10.6 g.). White powder. M.p. 161-163° C. TLC analysis. Conditions of analysis of ethyl and benzyl diester of BAPTA are analogous. One spot. $R_f$ 0.64 (Benzyl diester is plotted on TLC plate in solution in dimethylformamide).

$^1$H NMR [($CD_3$)$_2$SO], δ ppm): 4.02 (s, 4H), 4.18-4.19 (d, 8H), 4.97 (s, 4H), 6.73-6.94 (m, 8H), 7.22-7.32 (m, 10H).

Elemental analysis. $C_{36}H_{36}O_{10}N_2$. Calculated: C, 65.85%; H, 5.49%; N, 4.27%. Found: 65.56%, 5.83%, N; 4.12%.

2-(Dimethylamino)ethyl diester of BAPTA. Yield 70% (9.95 g.). White powder.

M.p. 126-127° C. TLC analysis. Silica gel 60 $F_{254}$ on aluminum sheet. Eluent: chloroform:methanol:water 60:40:2 v/v. One spot. $R_f$ 0.2.

$^1$H NMR ($CDCl_3$), δ (ppm): 2.57 (s, 12H), 2.60-2.63 (t, 4H), 3.60 (s, 4H), 3.75-3.78 (t, 4H), 4.06 (s, 4H), 0.11 (s, 4H), 6.68-6.85 (m, 8H).

Elemental analysis. $C_{30}H_{42}O_{10}N_4$. Calculated: C, 58.25%; H, 6.80%; N, 9.06%. Found: C, 57.94%; H, 6.90%; N, 8.97%.

Step 3a. Preparation of Sodium Salts of Diesters of BAPTA

Corresponding alkyl diester of BAPTA (0.019 Mol) is introduced into an Erlenmeyer flask (500 ml), equipped with a magnetic stirrer. About 250 ml of a mixture of methanol with water (1:1 v/v) is added to the ester. This mixture is vigorously stirred, because the ester is not dissolved in the solution. A concentrated solution of $NaHCO_3$ (0.038 mol, 3.19 g.) or concentrated solution of MeONa (0.038 mol) in water is added to the stirring mixture, and after 5-8 hours the mixture becomes transparent. This indicates that the alkyl diester is converted into disodium salt. Methanol and water are evaporated under vacuum. The obtained salt is dried by azeotropic distillation with ethanol and diethyl ether. Finally, the salt is dried under vacuum (5-6 mm Hg) for 8 hours.

Ethyl diester of BAPTA, disodium salt. White powder. Yield 95% (10.4 g.).

Elemental analysis. $C_{26}H_{30}O_{10}N_2Na_2$. Calculated: C, 54.16%; H, 5.21%; N, 4.86%, Na, 7.98%. Found: 54.10%; H, 5.27%; N, 4.65%; Na, 8.10%.

Propyl diester of BAPTA, disodium salt. White powder. Yield 95% (10.9 g.).

Elemental analysis. $C_{28}H_{36}O_{10}N_2Na_2$. Calculated: 55.63%; H, 5.63%; N, 4.63%; Na, 7.61%. Found: 54.76%; H, 6.13%; N, 4.46%; Na, 6.73%.

Butyl diester of BAPTA, disodium salt. White powder. Yield 95% (11.2 g.).

Elemental analysis. $C_{30}H_{38}O_{10}N_2Na_2$. Calculated: C; 56.96%, H; 6.01%, N; 4.43%, Na; 7.28%. Found: C; 56.50%, H; 6.00%, N; 4.20%, Na; 7.30%.

Heptyl diester of BAPTA, disodium salt. White powder. Yield 90% (10.3 g.).

Elemental analysis. $C_{36}H_{50}O_{10}N_2Na_2$. Calculated: C, 60.33%; H, 6.98%; N, 3.91%; Na, 6.42%. Found: C, 59.88%; H, 7.49%; N, 4.12%; Na, 6.76%.

Octyl diester of BAPTA, disodium salt. White powder. Yield 90% (15.7 g.).

Elemental analysis. $C_{38}H_{54}O_{10}N_2Na_2$. Calculated: C, 61.29%; H, 7.26%; N, 3.76%; Na, 6.16%. Found: C, 60.90%; H, 7.81%; N, 3.26%; Na, 6.52%.

Step 3b. Preparation of Calcium Salts of Diesters of BAPTA

The corresponding diester of BAPTA (1 g.) is dissolved in 1 L mixture of ethanol with water (70:30 v/v). The equivalent molal of $Ca(OH)_2$ is added to this solution. The obtained mixture is stirred by magnetic stirrer at room temperature for 24 hours. Then for the salts of ethyl, propyl and butyl diesters of BAPTA the solution is filtrated through Whatmann paper N1 and evaporated under vacuum (20-30 mm Hg) to dry. The precipitate is washed three times by diethyl ether (each portion is 100 ml) and dried under vacuum (2-3 mm Hg) at room temperature for 6 hours. For the calcium salts of heptyl and octyl diesters of BAPTA the ethanol solution is evaporated to dry. The precipitate is dissolved in 0.8 L of ethanol. The obtained mixture is filtrated through Whatmann paper N1 and then ethanol is evaporated under vacuum (20-25 mm Hg). The precipitate is washed three times by diethyl ether (each portion is 100 ml) and dried under vacuum (2-3 mm Hg) at room temperature for 6-7 hours.

Ethyl diester of BAPTA, calcium salt. White powder. Yield 90% (0.96 g.).

$C_{26}H_{30}N_2O_{10}Ca$. Calculated: C, 54.70%; H, 5.26%; N, 4.91%; Ca, 7.01%. Found: C, 54.32%; H, 5.40%; N, 4.81%; Ca, 6.81%.

Propyl diester of BAPTA, calcium salt. White powder. Yield 90% (0.98 g.).

$C_{28}H_{34}N_2O_{10}Ca$. Calculated: C, 56.19%; H, 5.68%; N, 4.68%; Ca, 6.69%. Found: C, 56.22%; H, 5.88%; N, 4.51%; Ca, 6.51%.

Butyl diester of BAPTA, calcium salt. White powder. Yield 90% (0.90 g.).

$C_{30}H_{38}N_2O_{10}Ca$. Calculated: C, 57.50%; H, 6.07%; N, 4.47%; Ca, 6.39%. Found: C, 57.18%; H, 6.24%; N, 4.28%; Ca, 6.11%.

Heptyl diester of BAPTA, calcium salt. White powder. Yield 80% (0.85 g.).

$C_{36}H_{50}N_2O_{10}Ca$. Calculated: C, 61.71%; H, 7.14%; N, 4.00%; Ca, 5.71%. Found: C, 61.44%; H, 7.24%; N, 4.18%; Ca, 6.31%.

Octyl diester of BAPTA, calcium salt. White powder. Yield 80% (0.83 g.).

$C_{38}H_{54}N_2O_{10}Ca$. Calculated: C, 61.79%; H, 7.32%; N, 3.79%; Ca, 5.42%. Found: C, 61.94%; H, 7.14%; N, 4.00%; Ca, 5.31%.

Example 2

Synthesis of BAPTA Diesters of Alkyl or Alkylaryl Ether of Mono-, Di- and Triethylene Glycol and Salts Thereof The procedure for synthesis of salts of alkyl or alkylaryl ethers of ethylene glycols is a four-step process similar to the procedure for preparation of the salts of the alkyl diesters of BAPTA.

Step 1. Preparation of BAPTA Anhydride

This first step of obtaining a BAPTA anhydride is identical to step 1 in the procedure for synthesizing the alkyl diesters of BAPTA as described above in Example 1.

Step 2. Synthesis of Monoalkyl Ethers of Mono-, Di- and Triethylene Glycol

The synthesis of monoalkyl ethers of mono-, di- and triethylene glycol is carried out according to following scheme:

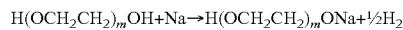

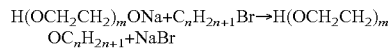

For example, m=1-3, n=5-18

About 0.8-0.9 g. of sodium (cut into small pieces where the diameter of each piece is 5-8 mm) are introduced, under argon atmosphere, into a double-neck round-bottom flask (250 ml), equipped with a reverse condenser and magnetic stirrer. Ethylene glycol (35 ml, 0.62 Mol) is added to the sodium, also under argon, and the flask is heated in oil bath at 70° C. with vigorous stirring. When most of the sodium is dissolved the rest of the sodium (typical quantity of sodium is 3.9 g., 0.17 Mol) is added piece by piece to the reaction mixture. It should be noted that sodium dissolution is accompanied by an increase in the temperature of the reaction mixture together with the increased reaction rate. In order to avoid explosion, it is necessary to add sodium slowly so that the reaction is well controlled. After all of the sodium is dissolved a drop funnel with the solution of the corresponding alkyl bromide (21.5 g., 0.12 Mol) in tetrahydrofuran (60 ml) is added to the reaction flask. The solution from the drop funnel is introduced drop-by-drop into the reaction flask. The temperature of the reaction mixture is kept at 70° C. Almost at once the precipitate of sodium bromide appears and increases in quantity in the course of the reaction. After 16 hours the reaction mixture is cooled to room temperature and about 150 ml of water is added to the organic solution. The product is extracted by two portions (40 ml each) of ethyl acetate. The combined ethyl acetate solution is washed with water and dried by sodium sulfate. The yellow solution of the product in ethyl acetate is discolored by heating with activated carbon. The colorless solution is separated from the carbon by filtration and the solvent is evaporated. The obtained product is distilled under vacuum and analyzed for its physical and chemical characteristics.

Monoheptyl ether of ethylene glycol. Colorless liquid. B.p. 95° C./1 mm Hg. Yield 70% (13.4 g.).

TLC analysis. Silica gel 60 $F_{254}$ on aluminum sheet. Eluent: ethyl acetate:n-hexane, 2:1 v/v. Indicator: 4-methoxybenzaldehyde (10 ml), ethanol (200 ml), 98% sulfuric acid (10 ml) and glacial acetic acid (2 ml). For indication the chromatogram is sprayed by the indicator spray and then it is charred at 350° C. One spot. $R_f$ 0.8.

$^1$H NMR (CDCl$_3$), δ (ppm): 0.84-0.90 (t, 3H), 1.27-1.33 (broad s, 8H), 1.55-1.61 (m, 2H), 2.25-2.30 (t, 1H, signal of OH-group, its position variable), 3.43-3.54 (m, 4H), 3.69-3.75 (m, 2H).

Heptyl ether of diethylene glycol. Colorless liquid. B.p. 100° C./1 mm Hg. Yield 70% (17.1 g.).

TLC analysis. Conditions of analyses of heptyl ether of mono- and diethylene glycol are analogous. One spot. $R_f$ 0.4.

$^1$H NMR (CDCl$_3$), δ (ppm): 0.84-0.90 (t, 3H), 1.27-1.32 (broad s, 8H), 1.55-1.61 (m, 2H), 2,71(t, 1H, signal of OH-group), 3.45-3.48 (t, 2H), 3.58-3.75 (m, 8H).

Heptyl ether of triethylene glycol. Colorless liquid. B.p. 107° C./1 mm Hg. Yield 70% (20.8 g.).

TLC analysis. Conditions of analyses of monoheptyl ether of mono- and triethylene glycol are analogous. One spot. $R_f$ 0.3.

¹H NMR (CDCl₃), δ (ppm): 0.84-0.90 (t,3H), 1.26-1.29 (broad s, 8H), 1.54-1.57 (m, 2H), 2.72 (t, 1H, signal of OH-group), 3.41-3.47 (t,2H), 3.58-3.74 (m, 12H).

Octyl monoethylene glycol. Colorless liquid. B.p. 60° C./0.5 mm Hg. Yield 85%.

TLC analysis. Conditions of analyses of dioctyl ether of ethylene glycol are the same as above. One spot. $R_f$ 0.7.

¹H NMR (CDCl₃), δ (ppm): 0.83-0.89 (t,3H), 1.25-1.27 (broad s, 10H), 1.54-1.57 (m, 2H), 2.39 (t, 1H), 3.41-3.52 (m,4H), 3.67-3.73 (m, 4H).

2-Benzyloxyethanol, 2-Dodecyloxyethanol, 2-(2-Dodecyloxyethoxy)-ethanol and 2-[2-(2-Dodecyloxyethoxy)-ethoxy]-ethanol were purchased from Fluka Co.

Step 3. Synthesis of BAPTA Diesters of Monoalkyl Ethers of Mono-, Di- and Triethylene Glycol The BAPTA anhydride of step 1 (1.5 g., 0.0034 Mol) and the corresponding monoalkyl ether of mono-, di- or triethylene glycol of step 2 (10-12 ml) are introduced, under argon atmosphere, into a round-bottom single-neck flask (50 ml), equipped with a reverse condenser and a magnetic stirrer. The mixture is heated in an oil bath at 115-120° C. with vigorous stirring. After 1-1.5 hours the mixture becomes transparent. Heating is continued for another 1.5 hours, till the reaction is completed. The flask is then cooled to room temperature and about 100 ml of petroleum ether (b.p. 60-80° C.) is added. The formed precipitate is extracted by centrifugation and washed three times with petroleum ether (40 ml each wash). The solid product is dried under vacuum for 5 hours and analyzed to verify the product characteristics, as exemplified for the following compounds:

BAPTA diester of methylethylene glycol. White solid M.p. 151-152° C. Yield 90% (1.81 g.).

TLC analysis. Silica gel 60 $F_{254}$ on aluminum sheet. Eluent is chloroform:methanol (1:1 v/v). For indication the chromatogram is sprayed by the indicator spray and then is charred at 100-150° C. Composition of indicator spray is 4-methoxybenzaldehyde (10 ml), ethanol (200 ml), 98% sulfuric acid (10 ml) and glacial acetic acid (2 ml). One spot. $R_f$ 0.14.

¹H NMR(CD₃OD), δ (ppm): 3.33 (s, 6H), 3.47-3.51 (t, 4H), 3.66 (s, 4H), 3.85 (s, 4H), 4.02-4.06 (t, 4H), 4.35 (s, 4H), 7.02-7.11 (m, 8H).

Elemental analysis. $C_{28}H_{36}O_{12}N_2$. Calculated: C, 56.76%; H, 6.08%; N, 4.73%. Found: C, 56.38%; H, 6.39%; N, 4.72%.

BAPTA diester of heptylethylene glycol. White solid. M.p. 111-112° C. Yield 90% (2.32 g.).

TLC analysis. Conditions of TLC analysis of BAPTA diester of methylethylene glycol and BAPTA diester of heptylethylene glycol are the same. One spot. $R_f$ 0.4.

¹H NMR [(CD₃)₂SO], δ (ppm): 0.81-0.86 (t,6H), 1.22 (broad s, 16H), 1,42 (m, 4h), 3.27-3.32 (m, 4H), 3.37-3.40 (m, 4H), 3.96-3.99 (m, 8H), 4.12 (s, 2H), 4.19 (s, 2H), 6.73-6.92 (m, 8H).

Elemental analyses. $C_{40}H_{60}O_{12}N_2$. Calculated: C; 63.16%, H; 7.90%, N; 3.68%. Found: C; 63.30%, H; 8.44%, N; 3.76%

BAPTA diester of octylethylene glycol. White solid. M.p. 121-122° C., Yield 80% (1.4 gr).

TLC analysis. Silica gel 60 on aluminum sheet. Eluent is chloroform:methanol (1:1, v/v). For indication the chromatogram is sprayed by the indicator spray and then is charred at 100-150° C. Composition of indicator spray is 4-methoxybenzaldehyde (10 ml), ethanol (200 ml), 98% sulfuric acid (10 ml), and glacial acetic acid (2 ml). One spot. $R_f$ 0.45.

¹H NMR (CDCl₃), δ (ppm) 0,84-0.89 (t, 6H), 1.26 (broad s, 20H), 1.51-1.57 (m, 4H), 3.37-3.42 (t, 4H), 3.53-3.56 (m, 4H), 3.96 (s, 4H), 4.03 (s, 4H), 4.17-4.21 (m, 4H), 4.37 (s, 4H), 6.87-6.94 (m, 4H), 7.03-7.09 (m,4H).

Elemental analysis. $C_{42}H_{64}N_2O_{12}$. Calculated: C, 63.96%; H, 8.12%; N, 3.55%. Found: C, 63.57%; H, 8.11%; N, 3.53%.

BAPTA diester of heptyldiethylene glycol. White solid. M.p. 95-96° C. Yield 85% (2.5 g.).

TLC analysis. Conditions of analysis of BAPTA diester of methylethylene and BAPTA diester heptyldiethylene glycol are the same. One spot $R_f$ 0.40.

¹H NMR [(CD₃)₂SO], δ (ppm): 0.81-0.86 (t 6H), 1.23 (broad s, 16H), 1.45 (m, 4H), 3.30-3.35 (m, 8H), 3.40-3.46 (m, 12H), 3.97-3.99 (m, 8H), 4.13 (s, 4H), 4.19 (s, 4H), 6.74-6.92 (m, 8H), 12.37 (s, 2H).

Elemental. $C_{44}H_{68}O_{14}N_2$. Calculated: C, 62.26%; H, 8.02%; N, 3.30%. Found: C, 6.47%; H, 8.42%; N, 3.40%.

BAPTA diester of heptyltriethylene glycol. White solid. M.p. 63-65° C. Yield 85% (2.7 g.).

TLC analysis. Conditions of analysis of BAPTA diester of heptyltriethylene glycol and BAPTA diester of methylethylene glycol are the same. One spot. $R_f$ 0.40.

¹H NMR [(CD₃)₂SO], δ (ppm): 0.81-0.87 (t, 6H), 1.23 (broad s, 16H), 1.45 (m, 4H), 3.31-3.36 (m, 4H), 3.42-3.48 (m, 20H), 3.97-3.99 (m,8H), 4.13 (s, 4H), 4.19 (s, 4H), 6.74-6.92 (m, 8H), 12.38 (s, 2H).

BAPTA diester of 2-benzyloxyethanol. White solid. Yield 80% (2.02 g.).

TLC analysis. Conditions of TLC analysis of BAPTA diester of 2-benzyloxyethanol and BAPTA diester of heptylethylene glycol are the same. One spot. $R_f$ 0.5.

¹H NMR [(CD₃)₂SO], δ (ppm): 3.43-3.47 (m, 4H), 3.97 (s, 4H), 4.00-4.03 (m, 4H), 4.12-4.16 (d, 8H), 4.40 (s, 4H), 6.70-6.93 (m, 8H), 7.23-7.30 (m, 10H).

MS(APCI, ammonium acetate), MH⁺ 746.1 (Calculated for MH⁺ 745.8).

BAPTA diester of 2-dodecyloxyethanol. White solid. Yield 80% (2.44 g.).

TLC analysis. Conditions of TLC analysis of BAPTA diester of 2-dodecyloxyethanol and BAPTA diester of heptylethylene glycol are the same. One spot. $R_f$ 0.5.

¹H NMR (CD₃OD), δ (ppm): 0.86-0.90 (t,6H), 1.27 (broad s, 36H), 150-1.56 (m, 4h), 3.39-3.44 (t, 4H), 3.50-3.53 (m, 4H), 3.65 (s, 4H), 3.85 (s, 4H), 4.01-4.05 (m, 4H), 4.33 (s, 4H), 6.87-7.11 (m, 8H).

MS (APCI, ammonium acetate), MH⁺ (902.1), calculated MH⁺ 902.2.

BAPTA diester of 2-(2-diodecyloxyethoxy)-ethanol. White solid. Yield 80% (2.68 g.).

TLC analysis. Conditions of TLC analysis of BAPTA diester of 2-(2-dodecyloxyethoxy)-ethanol and BAPTA diester of heptylethylene glycol are the same. One spot. $R_f$ 0.5.

¹H NMR (CD₃OD), δ (ppm): 0.88-0.93 (t, 6H), 1.28 (broad s, 36H), 1.51-1.60 (m, 4h), 3.44-3.49 (t, 4H), 3.54-3.61 (m, 12H), 3.66 (s, 4H), 3.84 (s, 4H), 4.04-4.07 (m, 4H), 4.35 (s, 4H), 6.68-7.13 (m, 8H).

MS(APCI, ammonium acetate) MH⁺ (989.7), calculated MH⁺ 990.2

BAPTA diester of 2-[2-(2-dodecyloxyethoxy)-ethoxy]-ethanol. White solid. Yield 70% (2.32 g.).

TLC analysis. Conditions of TLC analysis of BAPTA diester of 2-[2-(2-dodecyloxyethoxy)-ethoxy]-ethanol and BAPTA diester of heptylethylene glycol are the same. One spot. $R_f$ 0.5.

$^1$H NMR (CD$_3$OD), δ (ppm): 0.87-0.93(t, 6H), 1.29 (broad s, 36H), 1,52-1.57 (m, 4h), 3.42-3.47 (t, 4H), 3.53-3.74 (m, 24H), 3.83 (s, 4H), 4.03-4.07 (m, 4H), 4.36 (s, 4H), 6.91-7.13 (m, 8H).

MS (APCI, ammonium acetate), MH$^+$ (1078.8), calculated MH$^+$ 1078.4.

Step 4a. Preparation of Disodium Salt of BAPTA Diesters of Monoalkyl Ethers of Mono-, Di- or Triethylene Glycol.

The corresponding BAPTA diester of monoalkyl ether of mono-, di- or triethylene glycol (0.0025 Mol) is dissolved in methanol (arround 10 ml of alcohol is necessary for dissolving 1.0 g. of BAPTA diester) and the obtained solution is introduced into an Erlenmeyer flask (50 ml), equipped with a magnetic stirrer. A water solution of sodium bicarbonate (0.005 Mol in 2 ml) is added to a methanol solution of the BAPTA diester and the mixture is stirred for 2 hours at room temperature. The solvent is then evaporated under vacuum (30 mm Hg). The obtained precipitate is dried three times by azeotropic distillation with ethanol and two times with diethyl ether. Finally, the obtained product is washed with hexane and is dried under vacuum.

BAPTA diester of methylmonoethylene glycol, disodium salt. White solid.
Hygroscopic. Yield 95% (1.5 g.).
Elemental analysis. $C_{28}H_{34}O_{12}N_2Na_2$. Calculated: C, 52.80%; H, 5.35%; N, 4.40%; Na, 7.23%. Found: 52.20%; H, 5.59%; N, 4.49%; Na, 7.30%.

BAPTA diester of heptylmonoethylene glycol, disodium salt. White solid.
Hygroscopic. Yield 95% (1.9 g.).
Elemental analysis. $C_{40}H_{58}O_{12}N_2Na_2$. Calculated: C, 59.70%; H, 7.21%; N, 3.48%; Na, 5.72%. Found: C, 59.60%; N, 7.75%; N, 3.51%; Na, 5.51%.

BAPTA diester of heptyldiethylene glycol, disodium salt. White solid.
Hygroscopic. Yield 95% (2.1 g.).
Elemental analysis. $C_{44}H_{66}O_{14}N_2Na_2$. Calculated: C, 59.19%; H, 7.40%; N, 3.14%; Na, 5.16%. Found: C, 58.55%; H, 7.43%; N, 3.46%; Na, 5.49%.

BAPTA diester of heptyltriethylene glycol, disodium salt. White wax. Very hygroscopic. Yield 90% (2.2 g.).
Elemental analysis. $C_{48}H_{74}O_{16}N_2Na_2$. Calculated: C, 58.77%; H; 7.55%; N, 2.86%; Na, 4.69%. Found: C, 57.98%; H, 8.03%; N, 2.94%; Na, 4.64%.

BAPTA diester of octylethylene glycol, disodium salt. White solid. Yield 80%.
TLC analysis. Silica gel 60 on aluminum sheet. Eluent is chloroform:methanol (1:1, v/v). For indication the chromatogram is sprayed by the the indicator spray and then is charred at 100-150° C. Composition of indicator spray is 4-methoxybenzaldehyde (10 ml), ethanol (200 ml), 98% sulfuric acid (10 ml), and glacial acetic acid (2 ml). One spot. $R_f$ 0.45.

$^1$H NMR (CDCl$_3$), δ (ppm) 0,84-0.89 (t, 6H), 1.26 (broad s, 20H), 1.51-1.57 (m, 4H), 3.37-3.42 (t, 4H), 3.53-3.56 (m, 4H), 3.96 (s, 4H), 4.03 (s, 4H), 4.17-4.21 (m, 4H), 4.37 (s, 4H), 6.87-6.94 (m, 4H), 7.03-7.09 (m,4H).

Elemental analysis. $C_{42}H_{64}N_2O_{12}$. Calculated: C, 63.96%; H, 8.12%; N, 3.55%. Found: C, 63.57%; H, 8.11%; N, 3.53%.

BAPTA diester of 2-benzyloxyethanol, disodium salt. White solid. Hygroscopic.
Yield 90% (1.92 g.). Water content is 7.0%
Elemental analysis. $C_{40}H_{42}N_2O_{12}Na_2 \cdot 3H_2O$. Calculated: C, 57.01%; H; 5.70%; N, 3.33%; Na, 5.46%. Found: 56.44%; H, 5.90%; N, 3.49%; Na, 5.50%.

BAPTA diester of 2-dodecyloxyethanol, disodium salt. White solid. Hygroscopic.
Yield 90% (2.3 g.). Water content is 2.8%.
Elemental analysis. $C_{28}H_{34}N_2O_{12}Na_2 \cdot 1.5H_2O$ Calculated: C, 61.73%; H, 8.33%; N, 2.88%; Na, 4.73%. Found: 61.34%; H, 8.45%; N, 2.76%; Na, 4.99%.

BAPTA diester of 2-(2-dodecyloxyethoxy)-ethanol, disodium salt. White solid.
Hygroscopic. Yield 85% (2.35 g.). Water content is 4.3%.
Elemental analysis. $C_{54}H_{86}N_2O_{14}Na_2 \cdot 2.5H_2O$ Calculated: C, 60.15%; H, 8.51%; N, 2.60%; Na, 4.27%. Found: 59.68%; H, 8.33%; N, 2.46%; Na, 4.75%.

BAPTA diester of 2-[2-(2-dodecyloxyethoxy)-ethoxy]-ethanol, disodium salt.
White solid. Hygroscopic. Yield 85% (1.5 g.). Water content is 2.3%
Elemental analysis. $C_{58}H_{94}N_2O_{16}Na_2 \cdot 1.5H_2O$ Calculated: C, 60.66%; H; 8.45%; N, 2.44%; Na, 4.00%. Found: 60.20%; H, 8.32%; N, 2.32%; Na, 4.30%.

Step 4b. Preparation of Calcium Salt of BAPTA Diesters of Monoalkyl Ethers of Mono-, Di- or Triethylene Glycol.

The corresponding monoalkyl ether of mono-, di- or triethylene glycol diester of BAPTA (0.0025 Mol) is dissolved into 250 ml methanol. About 3-5 ml of water is added to this solution. The obtained solution is introduced into an Erlenmeyer flask (300 ml), equipped with a magnetic stirrer. The powder of CaH$_2$ (0.0025 Mol) is added to this solution with vigorous stirring. The stirring is continued for 3 hours at room temperature. After 3 hours the mixture is filtered through paper filter (Whatman N1) and the obtained solution is evaporated under vacuum (10-15 mm Hg). The precipitate is dried three times by azeotropic distillation with ethanol (each portion is 25-30 ml) and two times with diethyl ether. Finally, the product is washed with hexane and it is dried under vacuum (5 mm Hg) for 5 hours at room temperature.

Methylmonoethylene glycol diester of BAPTA, calcium salt. White powder Yield 90% (1.42 g.). $C_{28}H_{34}N_2O_{12}Ca$. Calculated: C, 53.33%; H, 5.40%; N, 4.44%; Ca, 6.35%. Found: C, 53.74%; H, 5.78%; N, 4.43%; Ca, 5.90%.

Heptylmonoethylene glycol diester of BAPTA, calcium salt. White powder. Yield 90% (1.79 g.). $C_{40}H_{58}N_2O_{12}Ca$. Calculated: C, 60.15%, H, 7.27%; N, 3.51%; Ca, 5.01%. Found: C, 60.32%, H, 7.63%, N, 3.54%; Ca, 4.59%.

Octylmonoethylene glycol diester of BAPTA, calcium salt White powder. Yield 90% (1.81 g.). $C_{42}H_{62}N_2O_{12}Ca$. Calculated: C, 61.01%; H, 7.50%; N, 3.38%; Ca, 4.84%. Found: C, 61.00%; H, 7.82%; N, 3.54%; Ca, 4.88%.

Heptyldiethylene glycol diester of BAPTA, calcium salt. White solid. Yield 80% (1.77 g.). $C_{44}H_{66}N_2O_{14}Ca$. Calculated: C, 59.59%; H, 7.44%; N, 3.16%; Ca, 4.51%; Found: C, 59.61%; H, 7.79%; N, 3.15%; Ca, 4.04%.

Methyltriethylene glycol diester of BAPTA, calcium salt. White solid. Yield 80% (1.61 g.). $C_{36}H_{50}N_2O_{16}Ca$. Calculated: C, 53.60%; H, 6.20%; N, 3.47%; Ca, 4.96%; Found: 53.95%; H, 6.33%; N, 3.20%; Ca, 4.73%.

Example 3

DP-BAPTA Reduces the Basal Activity as well as the TNFα-Induced Activity of MMP-9 in C6-Glioma Cells The effect of DP-b99 on MMP-9 activity was tested on cultured C6 glioma cells either in the absence (basal activity) or following treatment with Tumor Necrosis Factor alpha (TNFα) to induce gelatinases.

C6 rat glioma cells (ATCC; CRL-2199) grown on 100 mm petri dishes were detached by trypsinization and cultured to a density of $10^5$ cells/well on 24-well plates in DMEM+10% FCS. The TNFα-treated cells which were stimulated to induce gelatinases were incubated, on the next day after plating, for 18 hours in DMEM without serum in the presence of either 20 ng/ml or 40 ng/ml
TNFα (R&D, cat. #410-TRNC). Different concentrations of the tested compound, as indicated, in 0.48% fatty acid free BSA, 0.4% ethanol were added to the cells that were then incubated for a total of 18-24 hours at 37° C. Cells treated with vehicle only served as control group.

Conditioned media (CM) were then collected, centrifuged at 2000 rpm for 5 min., and supernatants were transferred to new tubes. MMP gelatinase activity was determined by using zymogram gels (Invitrogen, cat. #EC6175) which include gelatin as a substrate. Samples were loaded on gels in 62.5 mM Tris-HCl pH 6.8, 10% glycerol, 2% SDS and traces of bromophenol-blue. Gels were run in Tris/glycine-SDS running buffer, washed for 30 min. with renaturing buffer (Invitrogen) and for further 30 min. with developing buffer (Invitrogen). MMP activity was developed overnight at 37° C. with fresh developing buffer. The gels were then stained for one hour with Coomasie Blue (Brilliant Blue R, Sigma, cat. #B-8647) in 40% methanol and 7% acetic acid, and destained with 30% methanol/10% acetic acid. Digested gelatin areas formed by the MMPs (showed as clear bands) were photographed using Kodak digital Science™ Image station. Band analysis was determined using the Kodak digital Science™ 1D Image Analysis Software. Treatments were performed in triplicates and were subjected to three separate zymogram gels.

It was found that treatment with TNFα caused a 3- to 10-fold increase in MMP-9 activity. Added DP-BAPTAs (20 µM) inhibited both basal and TNFα-induced MMP activity in C6-glioma cells. Percentage inhibition on the basal and TNFα-induced MMP-9 activity was around 25% and up to 60%, respectively.

Example 4

DP-BAPTA Reduces Expression/Release of TNFα-Induced MMP-9 and Inhibits Enzyme Activity The effect of DP-b 109 on total amount of MMP-9 and its activity was tested in a human glioma cell line following treatment with Tumor Necrosis Factor alpha (TNFα).

A-172 human glioma cells (ATCC; CRL-1620) were grown and treated with 10 ng/ml TNFα in the presence of 0, 20 or 50 µM DP-b109 following the procedure as described above in Example 3. Cells treated with vehicle without the TNFα treatment, served as control groups.

CM from each treatment group was collected and subjected to zymogram gels (see procedure in Example 3), to MMP-9 immunoassay and to MMP-9 activity assay.

The total amount of MMP-9 protein was determined by immunoassay using the Quantikine™ (R&D Systems, U.S.A., Cat # DMP900) kit and following the manufacturer's instructions.

MMP-9 activity was assayed using the MMP-9 activity assay system (BioTrak™, Amersham, U.K., Cat. # RPN 2634), which quantifies the amount of the active MMP-9 form (see BioTrak kit instructions).

In FIG. 1A are shown the results of the immunoassay, where it is demonstrated that the amount of total MMP-9 is increased about 10-folds in the presence of TNFα. FIG. 1A demonstrates that DP-b109 reduces, in a dose-dependent fashion, the level of MMP-9 protein measured in the collected conditioned media. This reduction may be attributed to decrease in MMP-9 expression, to release of the enzyme or to combination of both.

Figure 1B:
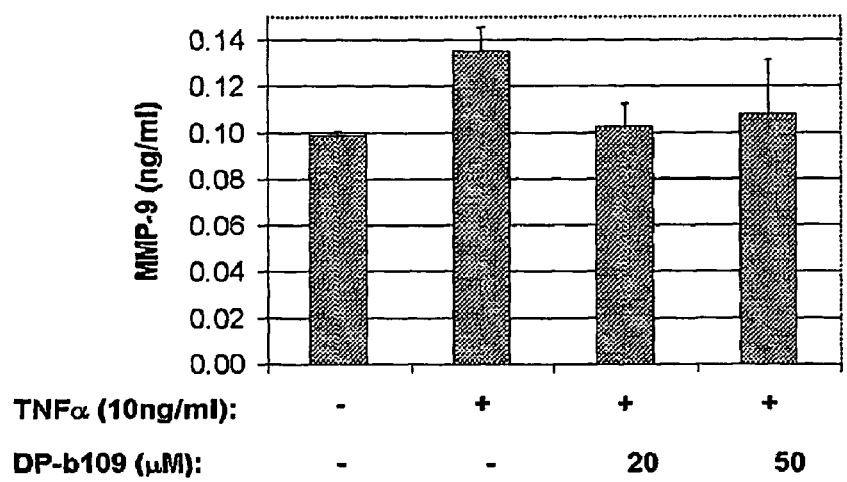

As can be seen in FIG. 1B, in the presence of TNFα there was a 35%-40% increase in active MMP-9. In the presence of the added DP-b 109, this increase was reduced to the baseline level, i.e. to the level of MMP-9 activity measured in the absence of the TNFα-induction.

Conclusions:

It was shown that the DP-BAPTA inhibitory effect on MMP-9 activity is in two levels: a) reduction of protein expression/release, and b) inhibition of MMP-9 enzymatic activity.

Example 5

DP-BAPTA Inhibits MMP-9 Activity Induced in C6-Glioma Cells by Either TNFα or PMA The effect of DP-BAPTA on MMP-9 activity induced with either TNFα or Phorbol 12-myristate 13-acetate (PMA) was tested in C6 glioma cells.

C6 glioma cells were grown and treated as described above in Example 3, except that cells were stimulated with either 20 ng/ml TNFα (R&D, cat. #410-TRNC) or 0.1 µM Phorbol 12-myristate 13-acetate (PMA, Sigma, cat. #P-8139).

It was shown that both TNFα and PMA increased MMP-9 secretion by about 10 fold. The results of an experiment where the effect of different concentrations of DP-109 was tested are shown in FIG. 2.

Figure 2A:
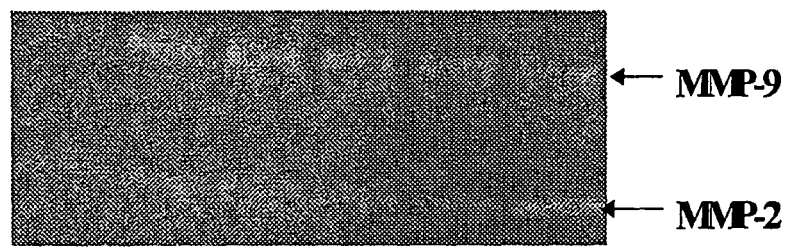
FIGS. 2A-B depict gelatin-zymogram gels used for detection of MMP-9 activity in conditioned media collected from cultured C6-glioma cells that were treated with 20 ng/ml TNFα (A) or 0.1 μM PMA (B), either in the absence or presence of different concentrations of DP-b109 as indicated. Areas of MMP-9 and MMP-2 protease activity, showed as clear bands, are marked with arrows.
Figure 2B:
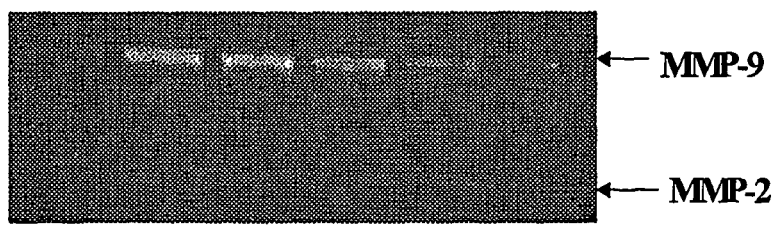

As can be seen in FIG. 2, DP-109 decreased the MMP-9 activity induced by either TNFα or PMA in a dose dependent fashion. The calculated $IC_{50}$ was similar for both treatments, $IC_{50}$=~10 µM.

These results obtained with two different stimulators of MMP-9; the known inducer of MMP-9 activity, TNFα, and the protein kinase C (PKC) activator, PMA, suggest that DP-BAPTA inhibitory effect on MMP-9 is not through an interaction with the TNFα receptor, but downstream to it, either by blocking the expression of MMP-9, or by direct inhibition of the MMP-9 enzyme activity.

Example 6

Effect of DP-BAPTA on MMP-9 Activity in Comparison to BAPTA and BAPTA-AM

Several DP-BAPTA molecules were screened for their effect on MMP-9 activity and were compared to the effect of the related chelating compounds 1,2-bis(2 aminophenoxy) ethane-N,N,N',N'-tetraacetic acid (BAPTA) and its lipophilic analog 1,2-bis(2-aminophenoxy)ethane-N,N,N',N'-tetra-acetic acid acetoxymethyl ester (BAPTA-AM).

C6 glioma cells were plated and treated with 20 ng/ml TNFα following the protocol described above in Example 3, either in the presence or absence of a tested compound as indicated. Each of the tested DP-BAPTAs, BAPTA or BAPTA-AM was added at the following final concentrations: 1, 5, 10 and 20 μM. As controls served cells treated with vehicle only.

Assays were performed in triplicates and zymogram analysis was carried out as described above in Example 3. $IC_{50}$ values for each of the tested DP-BAPTA compounds were calculated. The results are summarized in Table 1.

TABLE 1

Inhibitory effect on TNFα-induced MMP-9 activity

| Tested compound | R in formula I | $IC_{50}(\mu M)$ |
|---|---|---|
| vehicle | — | — |
| DP-b99 | $C_8H_{17}OCH_2CH_2$ | ~40 |
| DP-b109 | $C_{18}H_{37}OCH_2CH_2$ | 10–20 |
| DP-b460 | $C_{12}H_{25}OCH_2CH_2$ | 20 |
| DP-b458 | $C_{12}H_{25}(OCH_2CH_2)_2$ | n.d. |
| DP-b440 | benzyl-$OCH_2CH_2$ | 12 |
| BAPTA | H | No inhibition |
| BAPTA-AM | tetra-ester (acetoxymethyl) | Increased MMP9 activity | n.d.—not determined

Conclusions:

The most potent inhibitors among the tested compounds were 1,2-bis(2-aminophenoxy)ethane, N,N'-di(2-benzyloxy-ethyl acetate), N,N'-acetic acid, disodium salt [DP-b440] and 1,2-bis(2-aminophenoxy)ethane, N,N'-di(2-octodecyloxy-ethyl acetate), N,N'-diacetic acid, disodium salt [DP-b109] with calculated $IC_{50}$ of 12 μM and 10-20 μM, respectively.

It is important to note that the parent chelating compound, BAPTA, did not affect the MMP-9 activity. The related tetra-ester BAPTA analog, BAPTA-AM, increased rather than decreased the MMP-9 activity in the test model system used (C6 glioma cells stimulated with TNFα).

Example 7

DP-BAPTA Inhibits MMP-9 Activity in Primary Cultured Glial Cells

The effect of DP-BAPTA molecules on un-stimulated MMP-9 (basal activity) and their ability to inhibit MMP-9 activation induced by TNFα, was tested in primary glial cells.

Cortical glial cells from rat embryos (day 18 of pregnancy) were seeded on poly-D-lysine coated 24-well plates with MEM medium containing 5% FCS, 5% HS, 2 mM l-glutamine and 0.6% glucose, at a density of $5\times10^4$ cells/well. After 4 days in culture, the medium was changed to MEM+10% FCS. When glial cells reached confluence (around 17 days after plating), they were exposed for 24 hours to 10 ng/ml or 20 ng/ml human TNFα in order to induce MMP-9. The induction was performed either in the absence or presence of 25 μM DP-b99 (dilution 1:200 with medium from a stock of 5 mM in sodium citrate buffer) in a serum-free medium containing 5 mg/ml BSA (essentially fatty acid free). Conditioned media (CM) were collected and 12 μl of each of the triplicates was subjected to separate zymogram gels, as described above in Example 3.

A representative zymogram of MMP-9 activity in conditioned medium (CM) from control (un-stimulated) glial cells and from cultures treated with 10 or 20 ng/ml TNFα, either with or without DP-b99, is depicted in FIG. 3.

Figure 3A:
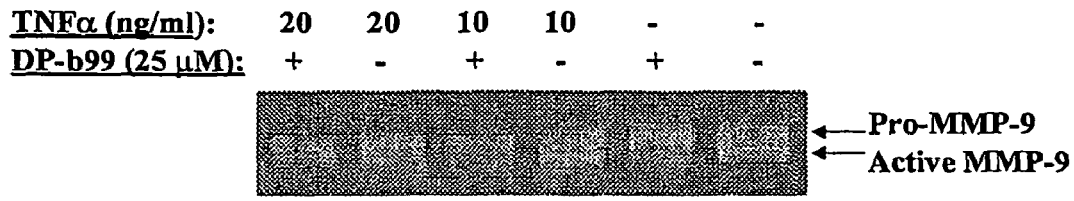
FIGS. 3A-C depict a representative gelatin-zymogram gel (3A) and analysis of biologically active MMP-9 (3B) and pro-MMP-9 (3C) forms of the enzyme. Conditioned media collected from C6-glioma cell cultures treated with 10 or 20 ng/ml TNFα, either in the absence (white bars) or presence (dark bars) of 25 μM DP-b99, as indicated, were run on zymogram gels. Arrows mark the pro- and active MMP-9 bands on the gel (3A). Band analyses (3B and 3C) were performed using the Kodak digital Science™ 1D Image Analysis software.

As can be seen in FIG. 3A, the two forms of MMP-9 were separated on the gel; the upper band represents the pro-MMP-9 with the higher molecular weight, while the lower band (lower MW) represents the biologically active form of the enzyme.

Figure 3B:
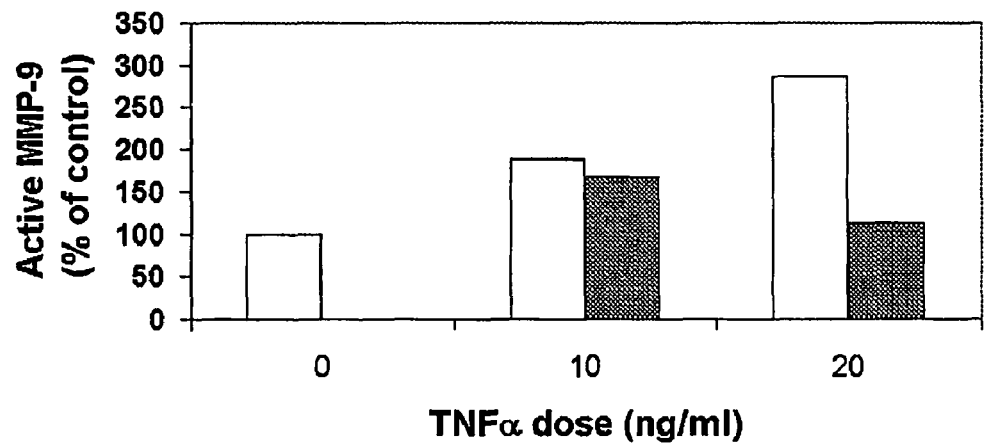
Figure 3C:
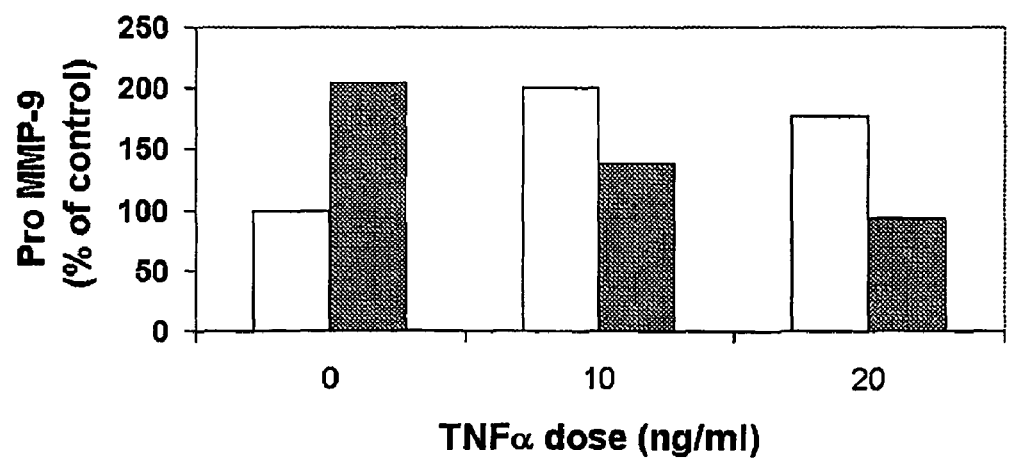

A quantitative analysis of the MMP-9 bands, representing the pro- and active forms of the enzyme, was performed on the triplicate zymograms. The results were normalized to percentage of control values (=100%) and are depicted in FIGS. 3B and 3C that represent, respectively, the biologically active- and pro-MMP-9 forms of the enzyme.

The results clearly demonstrated that in the un-stimulated cells DP-b99 increased the band intensity of pro-MMP-9 on the account of the active MMP-9 band, which was abolished. In the TNFα treated cells both pro- and active forms of MMP-9 were reduced.

Conclusions:

The DP-b99 inhibitory effect on basal MMP-9 activity in glial cells was demonstrated by showing an increase in band intensity of the Pro-MMP-9 on the account of the active MMP-9 form. In TNFα-treated cells, DP-b99 reduced both the pro- and active forms of the enzyme.

Example 8

Effect of DP-BAPTA on TNFα Release from Primary Glial Cells

The effect of various DP-BAPTA molecules on the levels of TNFα released in response to stimulation of primary glial cells with lipopolysaccharide (LPS) was measured.

Cortical rat glial cells were plated as described above in Example 7. When glial cells reached confluence (17 days after plating), they were exposed for 18 hours to 0.5 μg/ml LPS (E. coli 0111:B4, Calbiochem, cat. #437627) in the absence or presence of 20 μM DP-b99, DP-b109, DP-b458, DP-b440, DP-b460 or DP-b464 (=1,2-bis(2-aminophenoxy) ethane, N,N'-di{2-[2-(2-dodecyloxyethoxy) ethoxy]-ethyl acetate}, N,N'-diacetic acid) in a serum free medium. CM were collected and analyzed for the presence of TNFα by using an ELISA assay (DuoSet, R&D, cat. #DY510).

Figure 4:
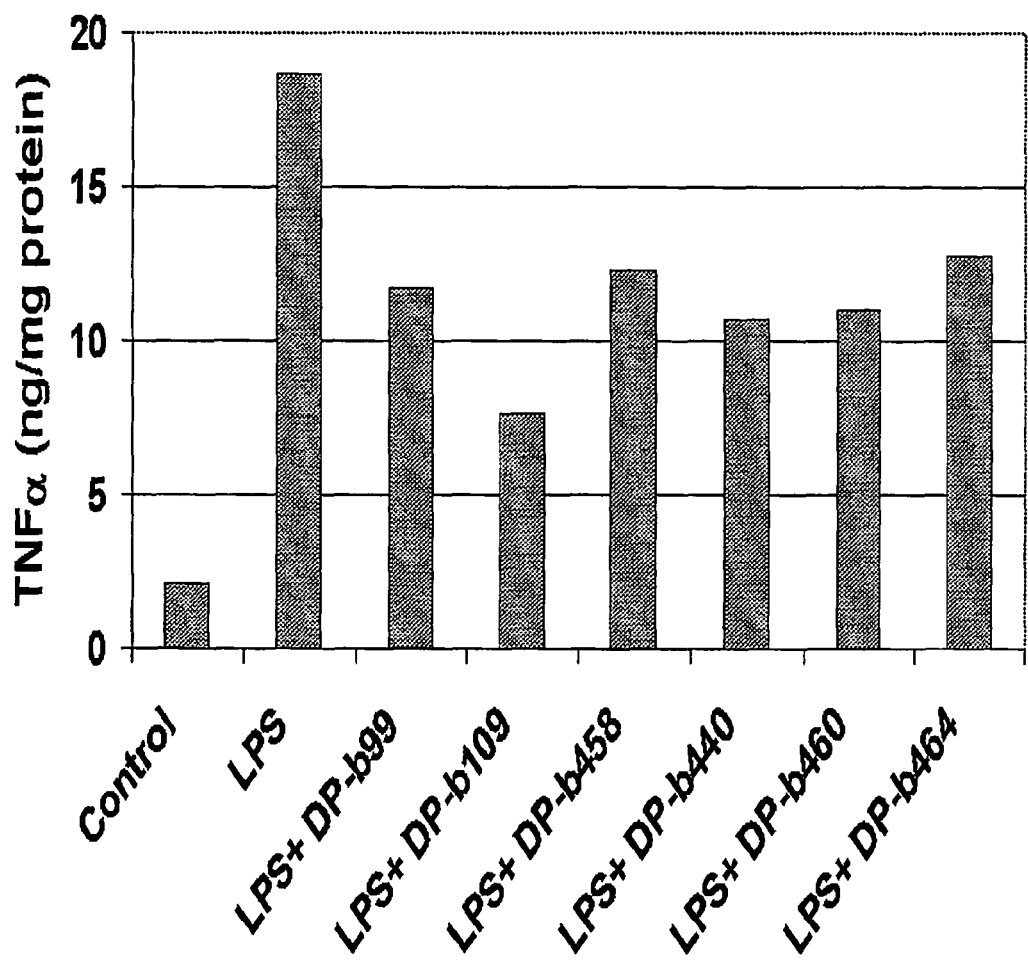
FIG. 4 depicts TNFα release from primary glial cells treated with 0.5 μg/ml LPS in the absence or presence of different DP-BAPTA compounds as indicated.

As can be seen in FIG. 4, LPS increased the release of TNFα by around 10 folds over control levels. All DP-BAPTA tested compounds inhibited this increase.

Conclusions:

The various DP-BAPTA compounds were effective to a different degree in their ability to reduce the induction of TNFα release in primary glial cells.

The results suggest a possible role for the DP-BAPTA molecules in blocking the activity of TNFα Converting Enzyme (TACE) in glial cells, hence implying a potential use of these molecules in inhibiting or interfering with neuro-inflammatory processes.

Example 9

Effect of DP-BAPTA on TNFα Release from Macrophages

The effect of DP-BAPTA on the levels of TNFα released in response to stimulation with lipopolysaccharide (LPS) is also tested in macrophage cell lines. Mouse macrophage cells grown on 100 mm petri dishes, are detached by scraping and re-cultured to a density of about $10^5$ cells/well on 24-well plates in DMEM+10% FCS. 48 hours later, cells are exposed for 18 hours to 0.5 µg/ml LPS (*E. coli* 0111:B4, Calbiochem, cat. #437627) in serum free medium in the absence or presence of 20 µM DP-BAPTA. Conditioned media are collected for TNFα analysis which is performed by using an ELISA assay (DuoSet, R&D, cat. #DY410).

The ability of various DP-BAPTA molecules to inhibit TNFα release from macrophages, may indicate a potential use of these molecules also in treating or ameliorating diseases and conditions related to peripheral inflammatory processes.

Example 10

Effect of DP-b99 on MMP-9 Activation In-Vivo

In order to test the effect of DP-BAPTA on MMP-9 activity in-vivo, the following model system for brain ischemia and the following protocol were employed.

Six Sprague-Dawley (SD) rats were subjected to unilateral (right hemisphere) Middle Cerebral Artery Occlusion (MCAO) for 2 hours. 5 µg/kg DP-b99 in 0.02% sodium citrate in saline was i.p. administered to three animals in a single dose, followed by 2 hrs. reperfusion. The other three animals were treated with vehicle instead of DP-b99. A rat that was only operated with no further treatment was used as a sham control.

The seven rats were sacrificed after 24 hrs. and each hemisphere of their brains was subjected separately to lysis and extracted for enzymatic activity. Brains were minced and solubilized in lysis buffer (25 mM Tris-HCl pH 7.5, 1% IGEPAL CA-630—a non-ionic detergent from Sigma, 100 mM NaCl, 0.5 U/ml aprotinin, 0.01% sodium azide) at a final concentration of 400 mg/ml. The preparations were incubated for 24 hrs. at 4° C. before lysates were centrifuged at 14,000 rpm for 15 min. and supernatants were collected.

Protein concentration was determined by the Bradford assay and 40 µg protein from each lysate were loaded on gelatin zymogram gels for determination of MMP-9 levels. Gels were developed for 48 hrs. Quantitative analysis of the gels was performed using the Kodak Digital System and Kodak 1D software as described in Example 3. The results are shown in FIG. 5.

Same level of MMP activity was measured in the two hemispheres of the sham-operated rat. In the MCAO-treated rats, as expected, induction of MMP-9 activity was demonstrated in the right (R-injured) hemisphere, while no significant increase was observed in the left (L-intact) hemisphere.

Figure 5A:
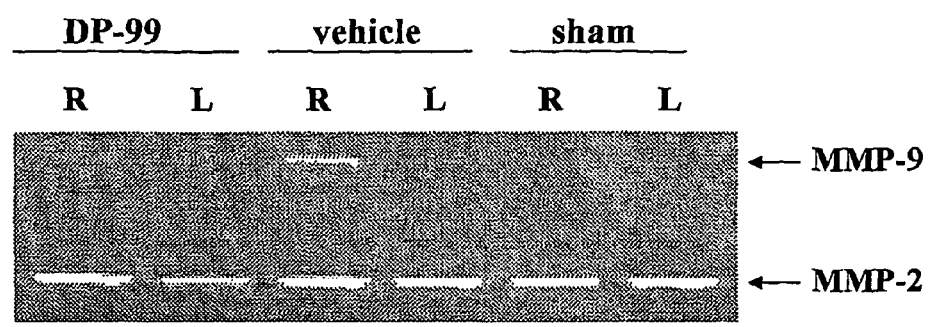
FIGS. 5A-B depict a gelatin-zymogram gel (A) and MMP-9 band analysis (B) of lysates of the right (R-injured) or left (L-intact) hemispheres from brains of unilateral MCAO treated rats. The animals were treated, 2 hours after reperfusion, with either 5 μg/kg DP-b99 or vehicle only, as indicated.
Figure 5B:
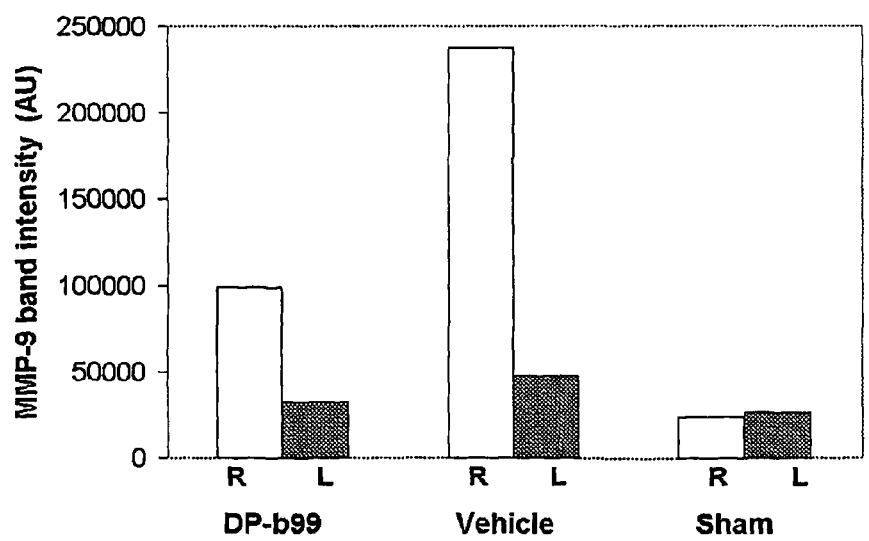

As shown in FIG. 5, treatment with DP-b99 inhibited this induction in MMP activity. Calculated R/L ratio in the DP-b99 treated rats was 3.0 in comparison to R/L=4.9 in the vehicle treated rats.

It is important to note that in contrast to MMP-9 that was inhibited by DP-b99, the activity level of the other tested gelatinase, MMP-2, was unaffected by the treatment with DP-b99.

Conclusions:

DP-b99 reduced the increase in MMP-9 activity induced by focal brain ischemia in rats. The results of this in-vivo study correlate with those of the in vitro experiments (Examples 3 to 7) that showed that DP-BAPTAs reduce MMP-9 activity induced in C6 and A-172 glioma cells and in primary glial cells. These findings indicate that DP-BAPTAs can inhibit MMP-9 activity in vivo, thus may be useful in interfering with damaging neuro-inflammatory processes.

Example 11

DP-b-99 Inhibits Calpain Activity in Primary Cortical Neurons

Calpain activity in primary cortical neurons was evaluated following activation of the enzyme by $H_2O_2$. Calpain activity was measured by monitoring proteolytic degradation of the calpain substrate α-spectrin, from the 280 kDa full-length protein to the 150 kDa degradation product.

Culture Preparation: Primary cortical neurons were prepared from the brains of embryonic day 16-17 (E16-17) rat fetuses. Cells from embryos of one mother were resuspended in 300 ml of "primary medium" (NBM Gibco, Glasgow, Scotland) with 0.5 mM glutamine, 0.4 units/ml penicillin, 0.4 µg/ml streptomycin, and B27 supplement (Gibco, Glasgow, Scotland), plus 25 µM glutamic acid. Cells ($\sim 3 \times 10^5$/ml) were seeded, 1 ml/well, in 24-well plate for viability assay, or 4 ml/well in 6-well plate for analysis of calpain activity. Every 3-4 days, half of the medium was replaced with fresh "primary medium". Cells were used for experiments after 5-7 days.

Induction of Oxidative Stress: $H_2O_2$ was added at the indicated concentrations to cells in "primary medium" from a solution of 10 mM that was prepared in PBS immediately before use. Viability was determined after 18 to 24 hours. DP-b99 was added to the medium 1-2 hours prior to induction of the oxidative stress.

Assay for Calpain activity: Primary cortical neurons in 6-well plates were lysed in 100 µL RIPA buffer (50 mM Tris pH 7.5; 150 mM NaCl; 0.5% DOC; 1% Triton X-100; 0.1% SDS; 1 mM Nappi; 2 mM EDTA) plus protease inhibitors (Bohringer, Manheim, Germany). After 10 min. incubation on ice, lysates were cleared by 15 min. centrifugation at 20,000 g at 4° C. Samples including 10-50 µg protein were separated on gradient 4-12% SDS-PAGE (Nu-PAGE, NOVEX, with MES buffer), and blotted to nitrocellulose paper according to the manufacture instructions. To detect the various forms of α-spectrin, blots were reacted with anti-spectrin antibodies (Affinity FG6090 1:1000), followed by HRP-second antibodies (Santa Cruz, USA), followed by ECL reaction (Amersham, Buckinghamshire, UK). Detection of bands was performed using the Image Station 440 (Kodak Digital System). The non-cleaved spectrin ran at ~280 kDa, while the calpain cleaved form ran at ~150 kDa. Quantitation of the bands was performed using the Kodak 1D software.

In the experimental system described above it was found that calpain-cleaved product appears after 2 hours and reaches a maximal level at 4 hours following addition of $H_2O_2$.

The effect of DP-b99 on calpain activity was studied 4 hours after addition of $H_2O_2$ by monitoring the $H_2O_2$-induced cleavage of spectrin. The cortical primary cells were pre-treated with DP-b99 (15 µg/ml) or with the commercially available calpain inhibitor MDL28170 (25 µM) for 1 hour before $H_2O_2$ (50 µM) was added. Calpain activity was determined by using the "Calpain activity" assay described above.

Figure 6:
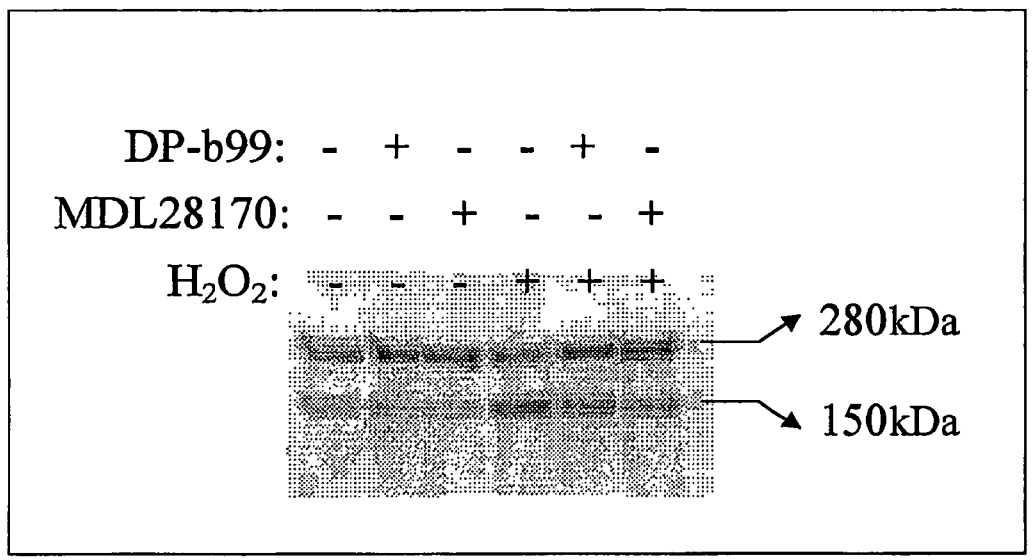
FIG. 6 depicts a Western blot of cortical primary cells lysates reacted with anti-spectrin antibodies as described in Example 11. The cells were pre-treated with either DP-b99 (15 μg/ml) or the commercial calpain inhibitor MDL28170 (25 μM) for one hour prior to induction of oxidative stress ($H_2O_2$, 50 μM) as indicated. The non-cleaved (280 kDa) and calpain-cleaved (150 kDa) forms of spectrin are marked by arrows.

As can be seen in FIG. 6, DP-b99 inhibited calpain activity to a similar extent as the known calpain inhibitor MDL28170. Percent inhibition by DP-b99 was from 40% to 60% in different experiments.

Conclusions:

DP-b99 inhibits $H_2O_2$-induced calpain activity similarly to the commercial calpain inhibitor MDL28170.

Example 12

DP-b-99 Inhibits Induced Spectrin Cleveage In Vivo

The effect of DP-b99 on calpain activity was further evaluated in vivo in transient focal cerebral ischemia model system in rats.

Transient middle cerebral artery (MCA) occlusion was performed in male Sprague Dawley (SD) rats by applying 4-0 silicone-coated nylon monofilament through external carotid artery. The animals were anesthetized with 4% halothane and maintained at 1.5% halothane in a 1:2 mixture of nitrous oxide and oxygen without tracheotomy and allowed to breathe spontaneously. Via a ventral cutaneous the common, right external and internal carotid arteries (ECA) were exposed. A suture was introduced into a ligated right external carotid artery, in a retrograde fashion towards the carotid bifurcation. It was then directed distally up to the right internal carotid artery to a distance of 20 mm from the carotid bifurcation to permanently occlude the origin of the MCA. It was secured with silk ligatures. Two hours after occlusion the monofilament was withdrawn to allow reperfusion and the cutaneous wound was sutured and cleaned. The whole procedure took about 25 min., with rectal temperature maintained throughout at 37° C.

DP-b99 was intraperitoneally (i.p.) administered in a single dose (5 μg/kg) at the start of reperfusion. MCAO-treated animals i.p.-injected with vehicle only served as control group. Four hours later, the animals were sacrificed and their brains were cut into two hemispheres and immediately frozen at –80° C.

Assay for Calpain activity: Each hemisphere was separately lysed by homogenization on ice in 5 ml RIPA buffer (50 mM Tris pH 7.5; 150 mM NaCl; 0.5% DOC; 1% Triton X-100; 0.1% SDS; 1 mM Nappi; 2 mM EDTA) plus protease inhibitors (Bohringer, Manheim, Germany). Lysates were cleared by 30 min centrifugation at 3,000 g at 4° C., followed by 30 min. centrifugation at 20,000 g at 4° C. Samples containing 50 μg protein were separated on gradient 4-12% SDS-PAGE (Nu-PAGE, NOVEX, with MES buffer), and blotted to nitrocellulose paper according to the manufacture instructions. To detect the various forms of α-spectrin, blots were reacted with anti-spectrin antibodies (Affinity FG6090 1:1000), followed by HRP-second antibodies (Santa Cruz, USA), followed by ECL reaction (Amersham, Buckinghamshire, UK). Detection of bands was performed using the Image Station 440 (Kodak Digital System). The intact spectrin ran at ~280 kDa, while the calpain-cleaved form ran at ~150 kDa. Quantitation of the bands was performed using the Kodak 1D software.

In the experimental system described above it was found that in animals subjected to MCAO, the calpain-cleaved spectrin (~150 kDa band) increased in the right (R, ischemic) hemisphere relative to the left (L, intact) hemisphere. In the sham-operated animals the amount of calpain-cleaved spectrin was similar in the two hemispheres.

The increase in the cleaved form of spectrin for each animal (n=2 for each treatment), was presented as the ratio between the 150 kDa—spectrin bands in the right (ischemic) and left (intact) hemispheres. The results are summarized in Table 2.

TABLE 2

Inhibition of increase in calpain-cleaved spectrin by DP-b99

| Treatment | Cleaved spectrin (R/L hemisphere) |
|---|---|
| Sham | 0.92 |
| ischemia + vehicle | 2.96 ± 0.26 |
| ischemia + DP-b99 | 1.42 ± 0.08 |

As shown in Table 2, the increase in calpain-cleaved spectrin in the right hemisphere relative to the left (R/L ratio) in the animals subjected to the unilateral MCAO and treated with vehicle only, was about 3 folds higher than the ratio in the sham-operated animals. In the animals treated with DP-b99, the increase in cleaved spectrin was much reduced; only about 50% increase over the sham-operated values.

Conclusions:

DP-b99 inhibits the increase in calpain activity induced by ischemia in vivo. Calpain inhibition by DP-b99 may be responsible, at least in part, for the neuroprotective effect exhibited by this molecule.

While the present invention has been particularly described, persons skilled in the art will appreciate that many variations and modifications can be made.

Therefore, the invention is not to be construed as restricted to the particularly described embodiments, rather the scope, spirit and concept of the invention will be more readily understood by reference to the claims which follow.

The invention claimed is:

1. A method for treating or managing a metalloproteinase (MMP) or calpain related disease or disorder in a mammal, the disease or disorder being glioma comprising administering to a mammal in need thereof, a pharmaceutical composition comrising a therapeutically effective amount of a compound of the general formula (I):

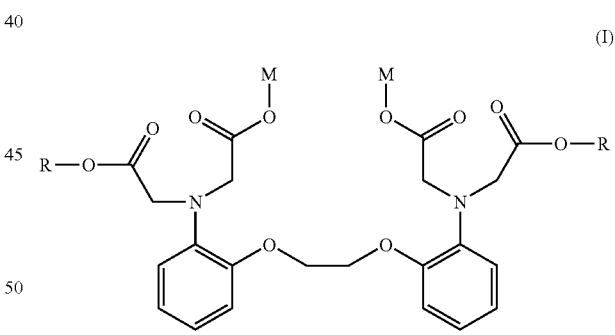

(I)

wherein
R is saturated or unsaturated alkyl, cycloalkyl, arylalkyl or cycloalkyl-alkyl radical having from 1 to 28 carbon atoms which may be interrupted by any combination of 1-6 oxygen and/or nitrogen atoms, provided that no two oxygen atoms or an oxygen and a nitrogen atom are directly connected to each other; and
M denotes a hydrogen or a physiologically acceptable cation.

2. The method according to claim 1 wherein said method further comprises treating mammal with additional therapeutic treatment.

3. The method according to claim 1, wherein said mammal is a human.

4. The method according to claim 1 wherein R in the compound of Formula (I) is a phenylalkyl, and alky interrupted by zero to three oxygen atoms, or a monoalkyl ether of mono-, di, or tri-ethylene glycol.

5. The method according to claim 1, wherein R in the compound of Formula (I) is selected from the group consisting of: $C_8H_{17}$, $C_8H_{17}OCH_2CH_2$, $C_{18}H_{37}$, $C_{18}H_{37}OCH_2CH_2$, benzyl-$CH_2OCH_2CH_2$, $C_{12}H_{25}OCH_2CH_2$, $C_{12}H_{25}(OCH_2CH_2)_2$ and $C_{12}H_{25}(OCH_2CH_2)_3$.

6. The method according to claim 1, wherein the metalloproteinase is MMP-9.

7. The method according to claim 2, wherein said additional treatment is selected from the group consisting of chemotherapy, irradiation therapy, immunotherapy, genetic therapy and surgery.

8. The method according to claim 1, wherein said compound of Formula (I) is selected from the group consisting of:
- 1,2-bis(2-aminophenoxy)ethane, N,N'-di(2-octoxyethyl acetate), N,N'-diacetic acid;
- 1,2-bis(2-aminophenoxy)ethane, N,N'-di(2-octodecyloxyethyl acetate), N,N'-diacetic acid;
- 1,2-bis(2-aminophenoxy)ethane, N,N'-di(2-benzyloxyethyl acetate), N,N'-acetic acid;
- 1,2-bis(2-aminophenoxy)ethane, N,N'-di(2-dodecyloxyethyl acetate), N,N'-diacetic acid;
- 1,2-bis(2-aminophenoxy)ethane, N,N'-di[2-(2-dodecyloxyethoxy)-ethyl acetate], N,N'-diacetic acid; and
- 1,2-bis(2-aminophenoxy)ethane, N,N'-di {2-[2-(2-dodecyloxyethoxy) ethoxy]-ethyl acetate}, N,N'-diacetic acid.

* * * * *